US007052454B2

(12) United States Patent
Taylor

(10) Patent No.: US 7,052,454 B2
(45) Date of Patent: May 30, 2006

(54) SEALED SURGICAL ACCESS DEVICE

(75) Inventor: Scott Taylor, Mission Viejo, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 55 days.

(21) Appl. No.: 10/399,057

(22) PCT Filed: Oct. 20, 2001

(86) PCT No.: PCT/US01/50160

§ 371 (c)(1),
(2), (4) Date: Apr. 11, 2003

(87) PCT Pub. No.: WO03/034908

PCT Pub. Date: May 1, 2003

(65) Prior Publication Data

US 2004/0054353 A1    Mar. 18, 2004

(51) Int. Cl.
*A61B 1/04* (2006.01)
(52) U.S. Cl. .................. 600/114; 600/208; 606/108; 606/213
(58) Field of Classification Search .............. 604/204, 604/206, 207, 208, 513, 264, 539; 606/1, 606/108, 213; 600/201, 204, 208, 210, 114
See application file for complete search history.

(56) References Cited

U.S. PATENT DOCUMENTS

| 4,984,564 A | 1/1991 | Yuen |
| 5,514,133 A | 5/1996 | Golub |
| 5,653,705 A | 8/1997 | de la Torre |
| 5,741,298 A | 4/1998 | MacLeod |
| 5,906,577 A | 5/1999 | Beane et al. |
| 6,033,426 A | 3/2000 | Kaji |
| 6,254,534 B1 | 7/2001 | Butler |
| 6,383,162 B1 | 5/2002 | Sugarbaker |
| 2002/0068923 A1 | 6/2002 | Caldwell |

(Continued)

*Primary Examiner*—Beverly M. Flanagan
(74) *Attorney, Agent, or Firm*—Richard L. Myers; Kenneth K. Vu; David G. Majdali

(57) ABSTRACT

A surgical access device is adapted to facilitate access through an incision in a body wall having an inner surface and an outer surface, and into a body cavity of a patient. The device includes first and second retention members adapted to be disposed in proximity to the outer surface and the inner surface of the body wall, respectively. A membrane extending between the two retention members forms a throat which is adapted to extend through the incision and form a first funnel extending from the first retention member into the throat, and a second funnel extending from the second retention member into the throat. The throat of the membrane has characteristics for forming an instrument seal in the presence of an instrument and a zero seal in the absence of an instrument. The first retention member may include a ring with either a fixed or variable diameter. The ring can be formed in first and second sections, each having two ends. Couplings can be disposed between the ends to accommodate variations in the size of the first retention member. The first retention member can also be formed as an inflatable toroid, a self-expanding foam, or a circumferential spring. A plurality of inflatable chambers can also provide the surgical access device with a working channel adapted for disposition across the body wall. A first retention member with a plurality of retention stations functions with a plurality of tethers connected to the membrane to change the shape of the membrane and the working channel. A stabilizing platform can be used to support the access device generally independent of any movement of the body wall.

23 Claims, 20 Drawing Sheets

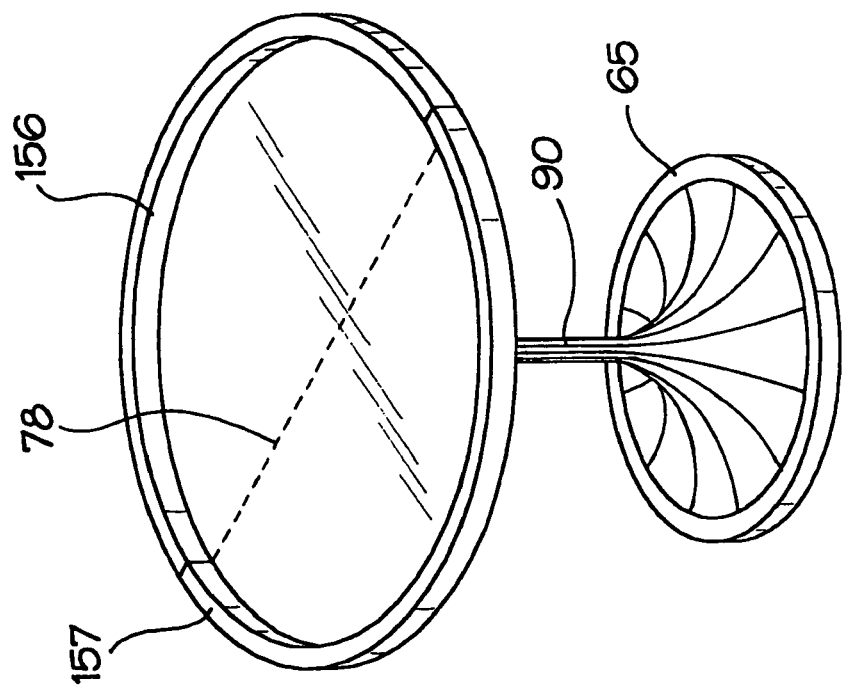
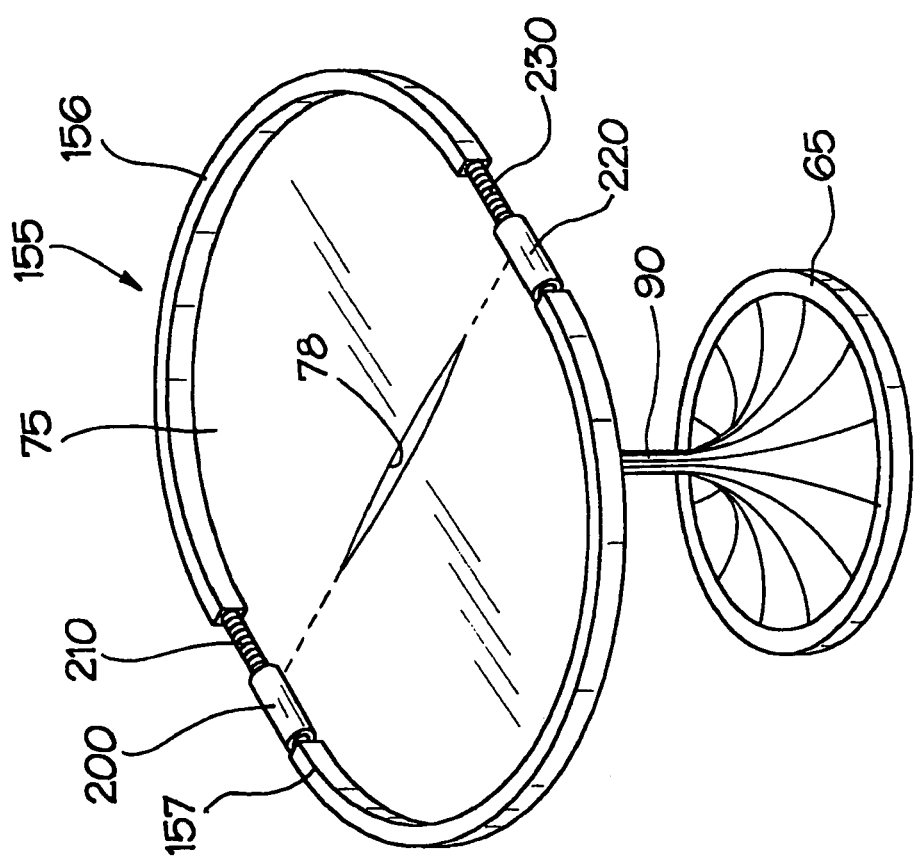

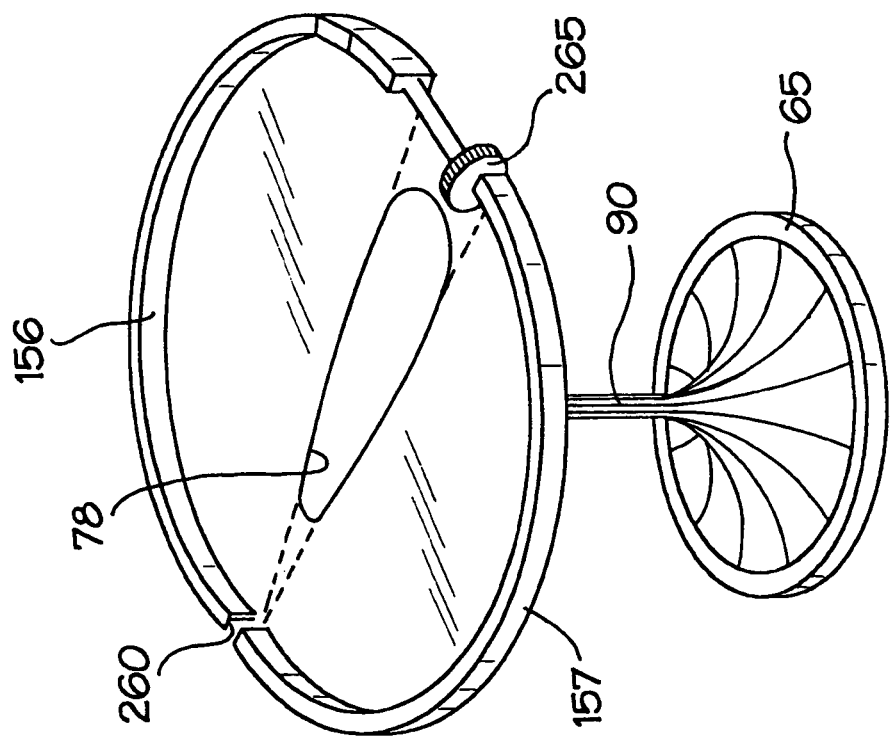
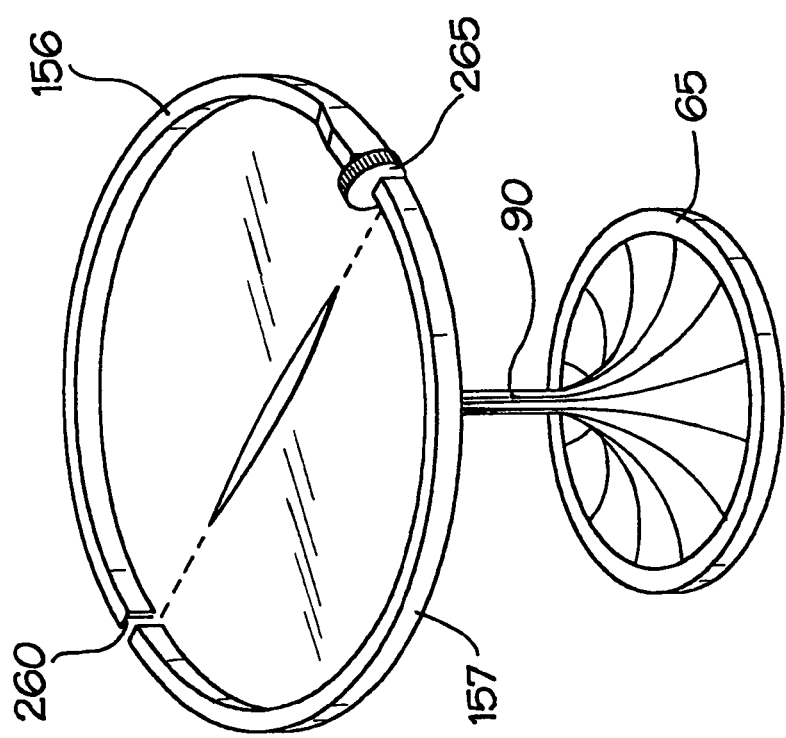

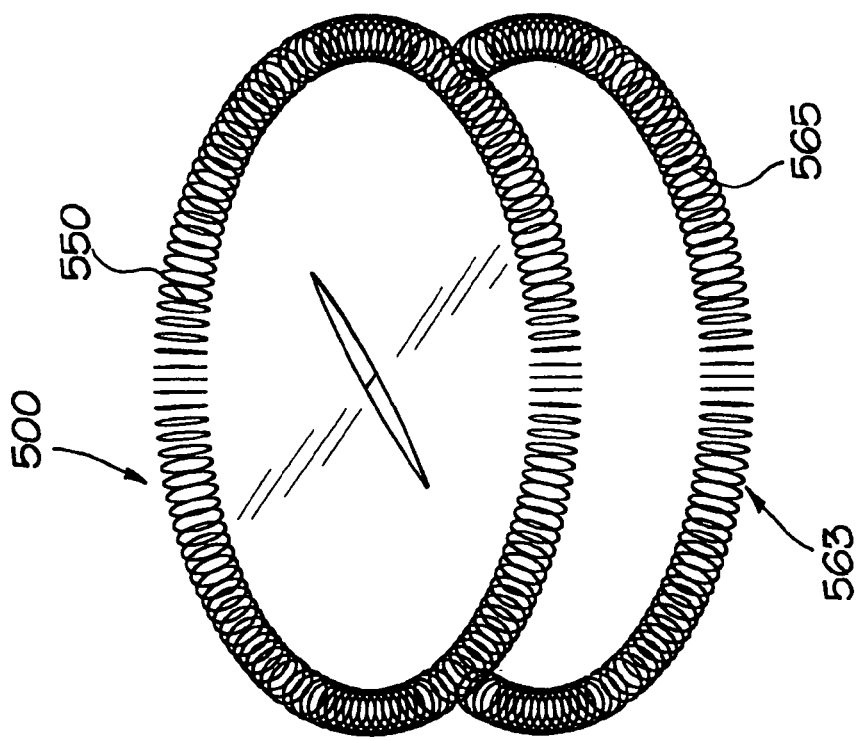
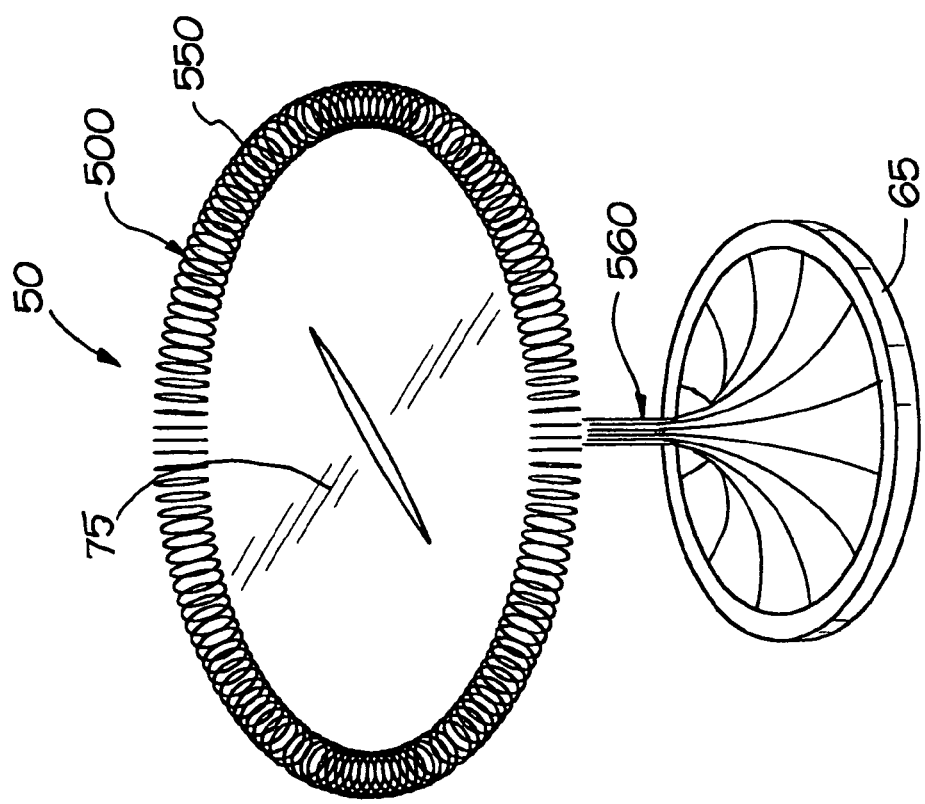

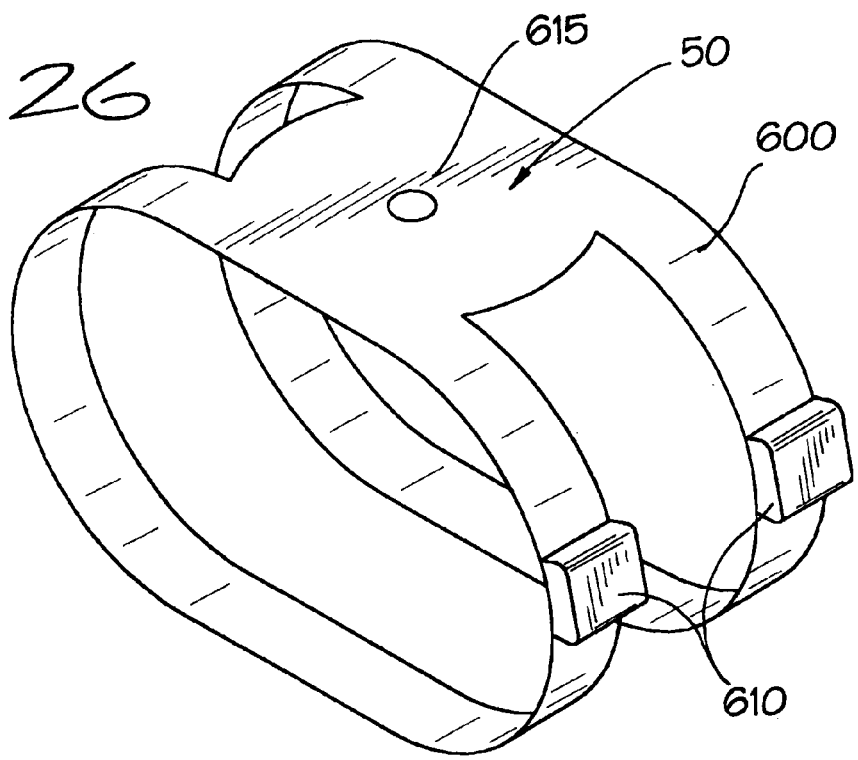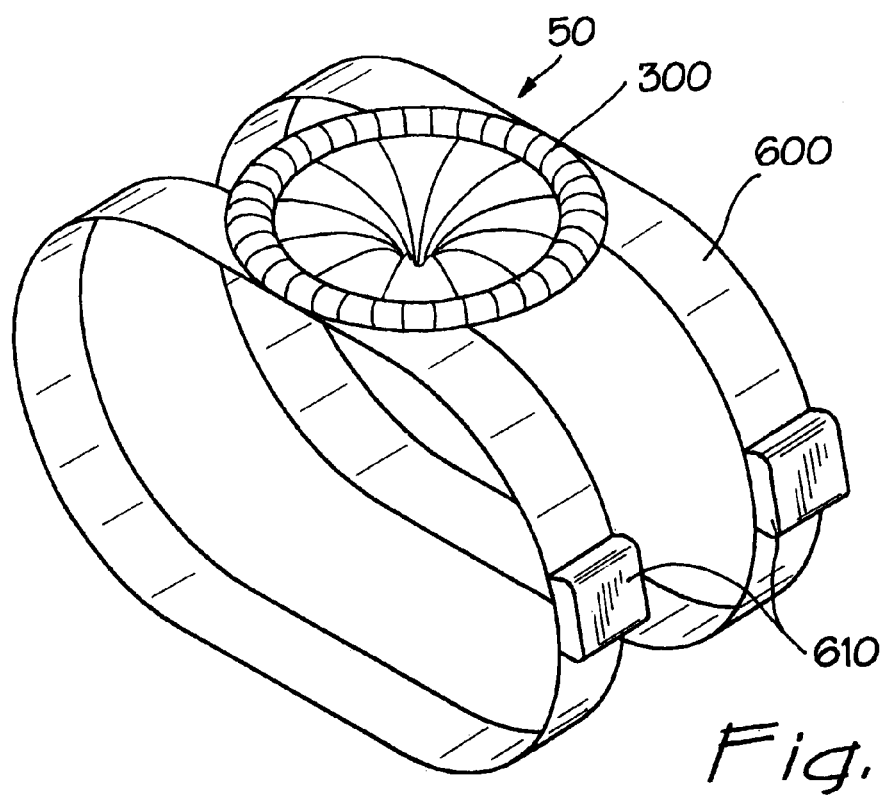

SEALED SURGICAL ACCESS DEVICE

CROSS REFERENCE TO RELATED APPLICATIONS

This is a non-provisional application claiming the priority of PCT application Ser. No. PCT/US02/50160, filed on Oct. 20, 2001, and entitled "Sealed Surgical Access Device," which is fully incorporated herein by reference.

BACKGROUND OF THE INVENTION

1. Field of Invention

This invention relates generally to surgical access devices, and more specifically to access devices adapted for use in minimal invasive surgery to provide sealed instrument access across a body wall and into a body cavity.

2. Discussion of Related Art

Surgical access to a body cavity, such as the abdominal cavity, is referred to as "open laparotomy" or "closed laparoscopy." An open procedure involves an incision of sufficient size to allow a surgeon to place hands and instruments within the surgical site. In addition, the site must be open enough for the surgeon to clearly see what he or she is doing. There is often a need for multiple retractors, clamps, and sponges. All of these devices compete for room within the surgical site.

Laparoscopic or closed surgery eliminates many of the issues surrounding open laparotomy. In a typical pressurized laparoscopy, the abdominal wall is punctured and at least one trocar is inserted into the peritoneum. Gas is introduced into the abdominal cavity and to elevate the abdominal wall away from the internal organs. This results in a large, clear operating field. Additional trocars can be inserted as needed for various procedures. A laparoscope is used to provide visualization of the surgical site. The instrumentation for laparoscopic procedures has developed prolifically in recent years and the surgeons have become comfortable with a "remote-control" approach to various aspects of surgery. Cutting, dissecting, cauterizing, stapling and suturing have all been addressed by laparoscopic device manufacturers.

Despite the many advantages of laparoscopic surgery, there remain a few complex procedures that make laparoscopy difficult or risky. In some of these cases, a hybrid procedure makes the most sense. If one could have the visibility and open field of a laparoscopic procedure and the control of an open procedure, one would truly have it all. However, the two modalities tend to obviate each other. Indeed, there are some who would argue that the advances of laparoscopy would be in vane if an open procedure were added as a default.

In recent years, a few enterprising surgeons have advanced a method that they call "hand-assisted" laparoscopy or "handoscopy." This involves placing one of the surgeon's hands inside the patient through an enlarged incision, while under laparoscopic visualization. With no protruding instrumentation normally used in closed laparoscopy, it is not required to perform overly challenging maneuvers The challenge now facing the surgeon in this procedure is providing an adequate sealing means within the enlarged incision. The surgeon's hand must be comfortable, properly placed and free to move with a normal range of motion. In addition, the surgeon should be able to remove and replace his/her hand into the abdominal cavity without loss of pneumoperitoneum.

Several devices have been proposed in an attempt to satisfy the requirements of the "handoscopist." They generally involve an elastomeric seal that fits through an incision and is held in place by retention means on either or both sides of the abdominal wall. The devices are generally complex and require several steps to place. One of the devices requires an adhesive to be placed on the exterior abdominal wall (skin) as the seal is adhered to the skin. This requires not only application of the adhesive but also a drying time. Allergic reactions and other complications must be considered when using this product. Another device makes use of a "toroidal balloon" that inflates to position the device and seal the incision. The surgeon must overcome the friction and sealing pressure of this device when inserting and withdrawing his/her hand from the surgical site. A further device involves the use of a built-in glove or sleeve. This arrangement diminishes the range of motion and the tactile sensation of the hand.

U.S. Pat. No. 5,848,992 discloses a surgical access device that allows the conversion of an open procedure to a laparoscopic procedure. In addition, the '992 patent discloses the use of such a device in a case where a large organ is to be removed. In this instance, an incision of adequate size is made initially and sealed with the device at the same time the trocars are being inserted Notwithstanding these proposed devices, there remains a continuing need for a surgical access device that provides a flexible, simple and complete seal within an incision of adequate size for introduction of a human hand.

SUMMARY OF THE INVENTION

The present invention satisfies the requirements of a surgical access device for use with surgical instruments including the surgeon's hand. With this access device, "hand-assisted" laparoscopy is greatly facilitated within a closed surgical environment.

The present invention makes use of an internal retention member and an external retention member connected by a flexible, lubricious material. At least one of the retention members is tensionable to provide adequate stability to the incision site.

The present invention also provides a sealing portion that allows the largest range of hand motion without leakage of insufflation gas. The seal is formed of a material that responds well to the presence of glove material such as Natural Latex, Poly-isoprene, Nitrile, Vinyl or Polyurethane.

In one aspect of the invention, the surgical access device is adapted to facilitate access through an incision in a body wall having an inner surface and an outer surface, and into a body cavity of a patient. The device includes a first retention member configured to surround the incision in proximity to the outer surface of the body wall. A second retention member is configured to surround the incision in proximity to the inner surface of the body wall. A membrane extending between the first retention member and second retention member forms a throat adapted for disposition through the incision. A first funnel extends from the first retention member into the throat and a second funnel extends from the second retention member into the throat. The throat of the membrane has characteristics for forming an instrument seal in the presence of an instrument, any zero seal in the absence of an instrument.

In another aspect of the invention, the first retention member comprises a ring having a first section with a first end and a second end, and a second section with a third end moveable relative to the first end to the first retention member and a fourth end moveable relative to the second end of the first retention member. A coupling is disposed between the first end of the first retention member and the third end of the second retention member. This coupling is operable to vary the distance separating the first end and the third end to control the shape of a working channel formed by the membrane. A second coupling or a hinge may be provided between the second end of the first retention member and the fourth end of the second retention member.

In a further aspect of the invention, the first retention member has a shape that is variable to control the shape of the working channel formed by the membrane. The first retention member can be formed as an inflatable structure such as a toroid. The first retention member may also include self expanding foam for a circumferential spring.

In still a further aspect of the invention, a surgical access device can include a plurality of inflatable chambers each extending in a plane passing through the axis of the device. These chambers collectively define a working channel that is adapted for disposition across the body wall. The chambers may have a straight or U-shaped configuration.

In another aspect of the invention, the device includes a first retention member including a ring with a plurality of retention stations. The membrane is attached to a plurality of tethers that can be coupled to the ring at an associated one of the retention stations to provide the membrane with a desired shape.

In still a further aspect of the invention, a stabilizing platform is proposed to support the access device generally independent of any movement associated with the body wall.

These and other features and advantages of the invention will become more apparent with a description of preferred embodiments in reference to the associated drawings.

DESCRIPTION OF DRAWINGS

FIG. 9 shows an adjustable external retention member opening the seal portion;

FIG. 10 shows the adjustable retention member with a seal portion under minimum tension;

FIG. 11 illustrates an adjustable retention having a hinge and jackscrew combination:

FIG. 12 shows the hinge and jackscrew placing opening tension on the seal member;

FIG. 24 illustrates an alternate embodiment wherein the external retention member is a coil spring;

FIG. 25 illustrates the alternate embodiment wherein the external and the internal retention members are coil springs;

FIG. 26 illustrates an alternate embodiment of the present invention wherein a strap is used to maintain a position over a surgical incision;

FIG. 27 illustrates an embodiment of the present invention wherein preferred embodiments of the retention member and the seal member are held in place by a strap;

DESCRIPTION OF PREFERRED EMBODIMENTS AND BEST MODE OF THE INVENTION

Figure 1:
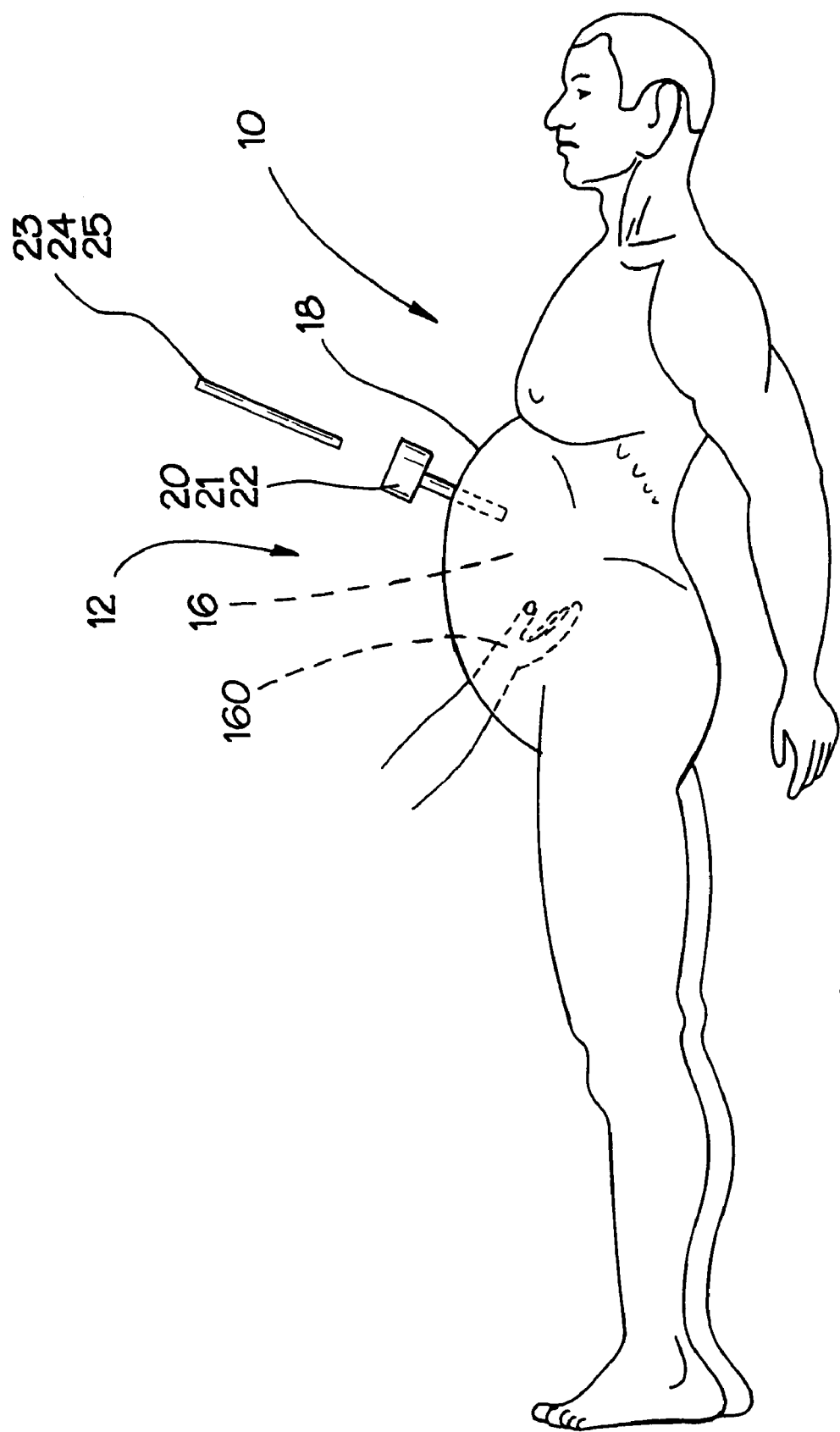
FIG. 1 is a side view drawing of a surgical patient in a laparoscopic procedure.

In FIG. 1, a patient is illustrated in a prone or supine position and designated by the reference numeral 10. The patient 10 has an abdomen 12 which includes a body or abdominal cavity 16 defined by an abdominal wall 18. A plurality of trocars 20, 21, and 22 are placed so as to provide surgical access to the abdominal cavity 16. Various instruments 23, 24, 25 are illustrated for use through the trocars 20, 21, and 22.

Figure 2:
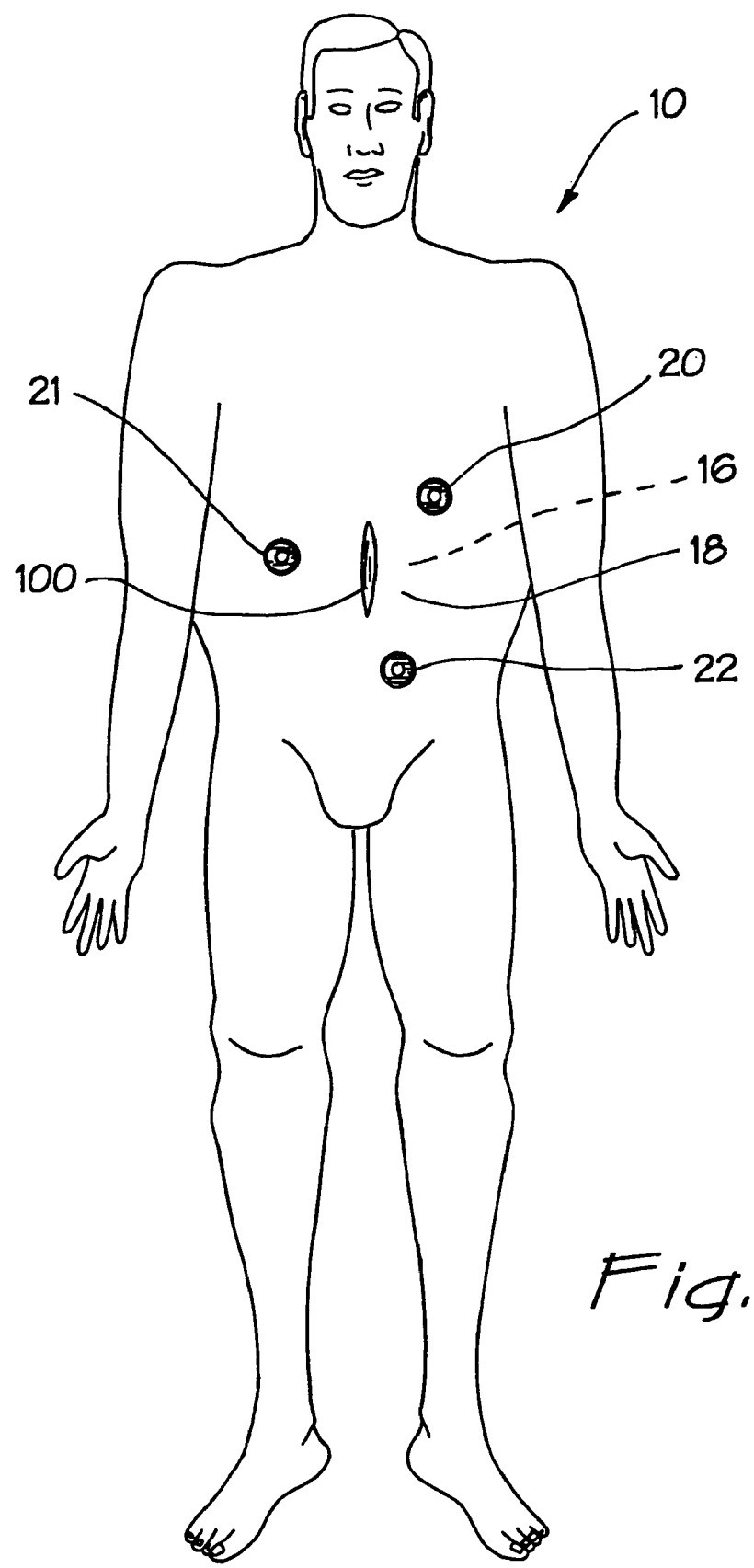
FIG. 2 is a front view drawing of a surgical patient in a "hand-assisted" surgical procedure.

In FIG. 2, a "hand-assisted" laparoscopic procedure is shown. The patient 10 is supine and the abdominal cavity 16 is insufflated. In addition to the trocars 20, 21, and 22, there is an additional surgical access device 50 that has been placed relative to a surgical incision 100. This access device 50 is adapted to receive a hand 160 of a surgeon, as it is placed through the access device 50 and into the abdominal cavity 16 of the patient 10. The surgeon is able to use the inserted hand 160 to perform tasks that are too difficult or not safe for the instruments normally used in laparoscopy. The access device 50 provides a gas tight seal so that the insufflated, pressurized abdomen at cavity 16 does not collapse. The access device 50 may also accommodate large, contaminated specimens or diseased organs or tissue. Furthermore, instrumentation or tools that might otherwise be too large for a trocar may be introduced through the access device 50 and subsequently attached to device drivers operated through the trocars 20, 21, and 22. Specimen bags that are introduced through a trocar may be removed through the access device 50 when fully burdened.

Figure 3:
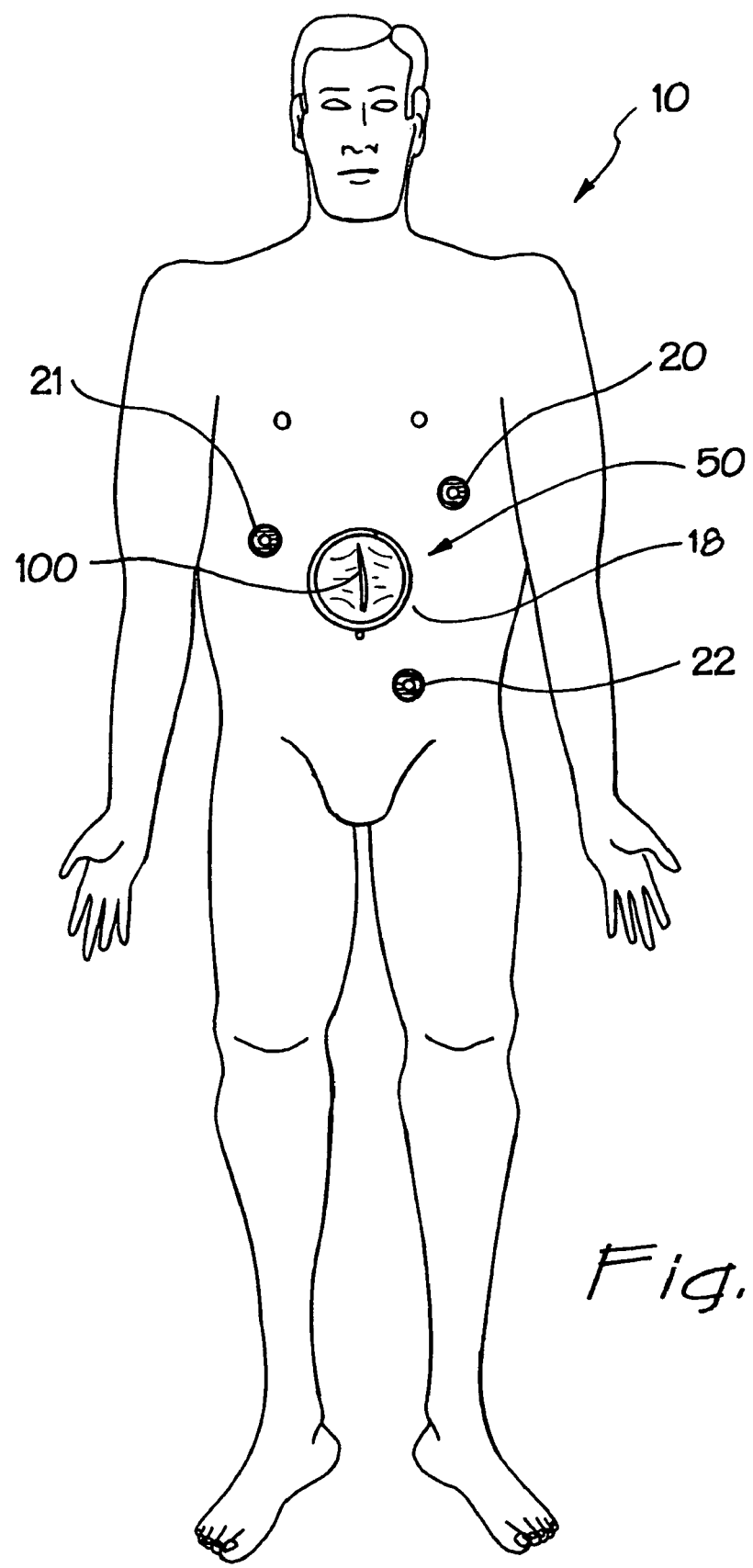
FIG. 3 is a front view drawing of a preferred embodiment of the present invention in place.

The access device 50 is placed through the surgical incision 100, FIG. 3, and retained against the external abdominal wall 17 by a first retention member or retainer 55, and against the internal abdominal wall 18 by a second retention member or retainer 65. The external, first retainer 55 supports a gas tight sleeve or membrane 75 at a first end 76. The internal, second retainer 65 supports the gas tight sleeve or membrane 75 at the second, opposite end 86. The two opposing ends 76 and 86 maintain a communicating surface 77 that passes through the incision 100. The material of the surgical access device 50 provides a durable and non-permeable surface against the incised tissue defining the incision 100.

Figure 4:
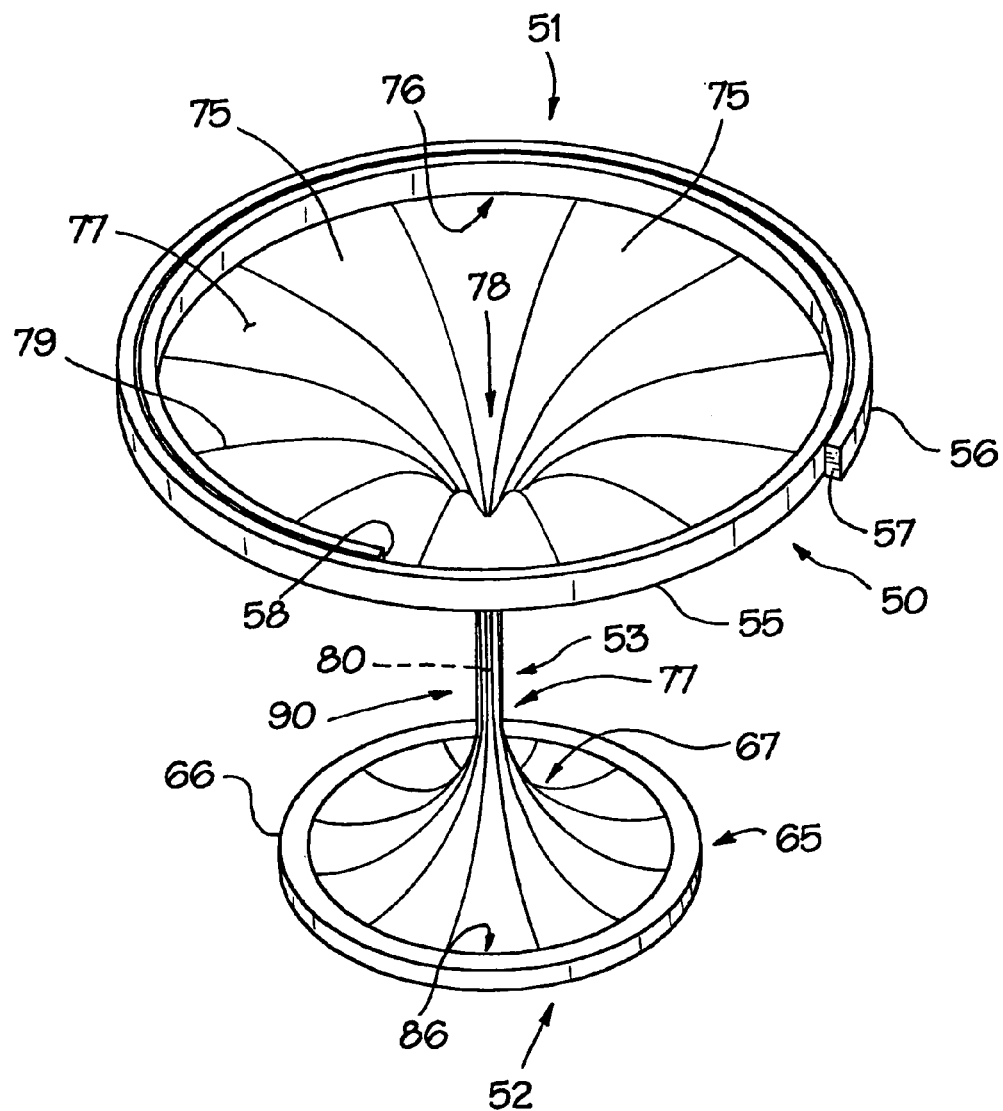
FIG. 4 is an oblique view drawing of the present invention showing two retention members.
Figure 6:
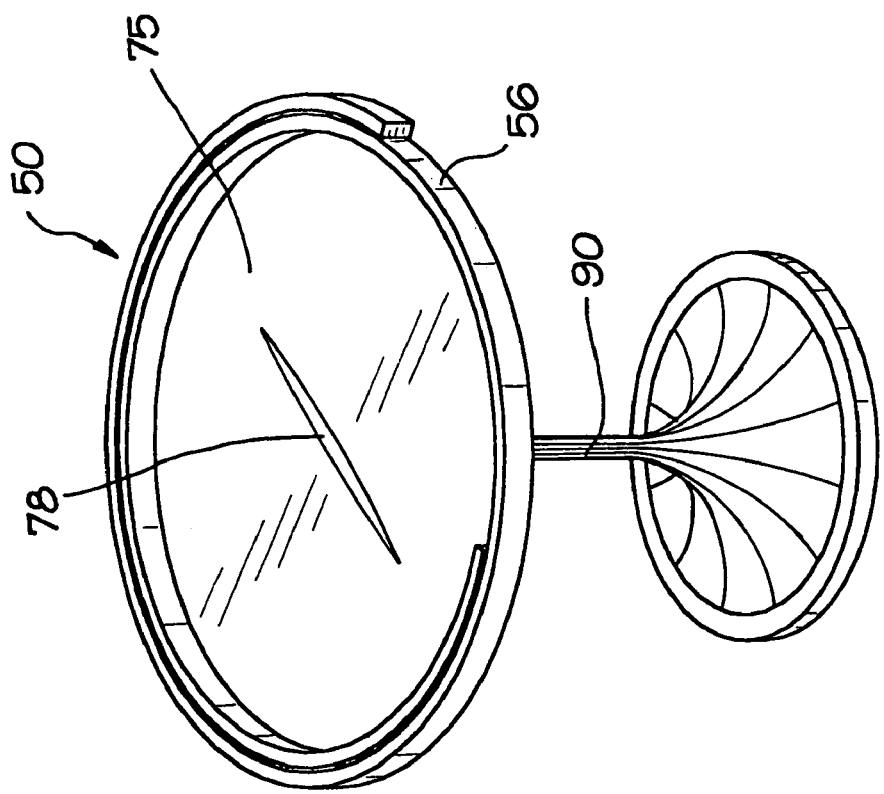
FIG. 6 shows the present invention having an alternate exterior retention member.
Figure 5:
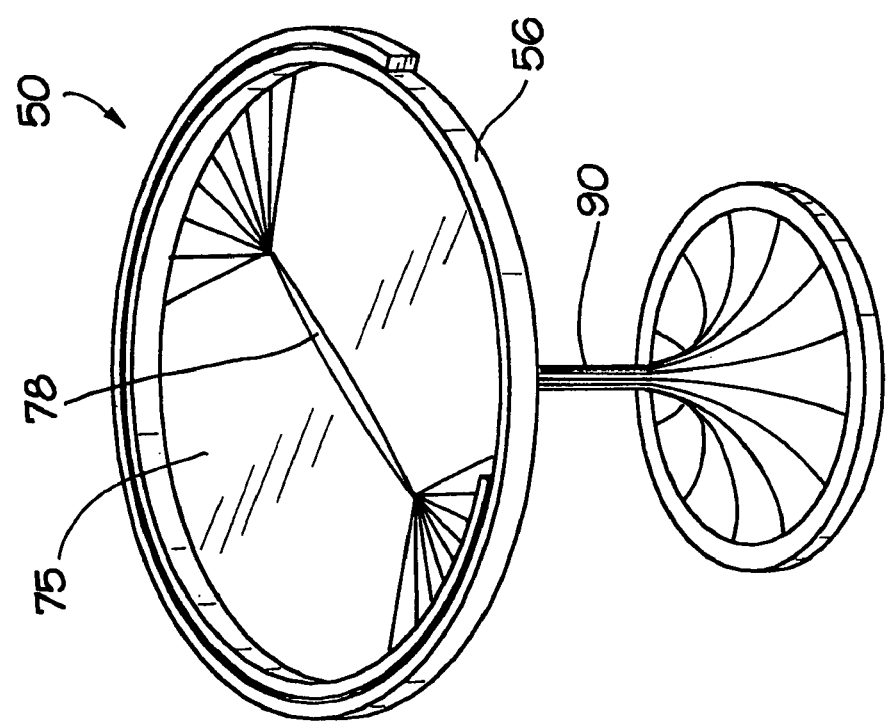
FIG. 5 is an oblique view drawing of the invention in an alternate embodiment.
Figure 7A:
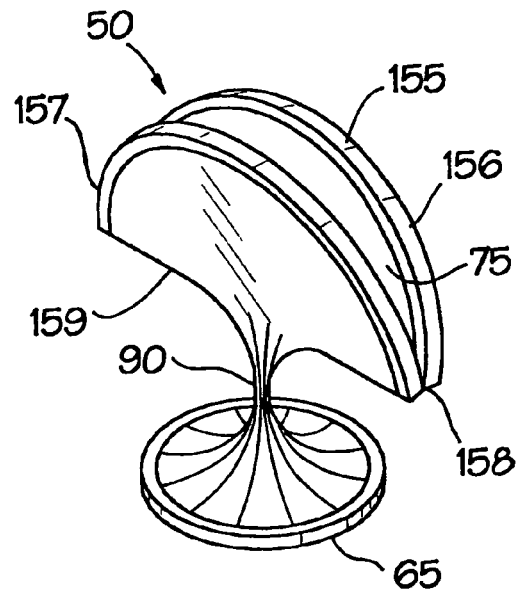
FIG. 7A illustrates a folded retention member of the present invention in a closed condition.
Figure 7B:
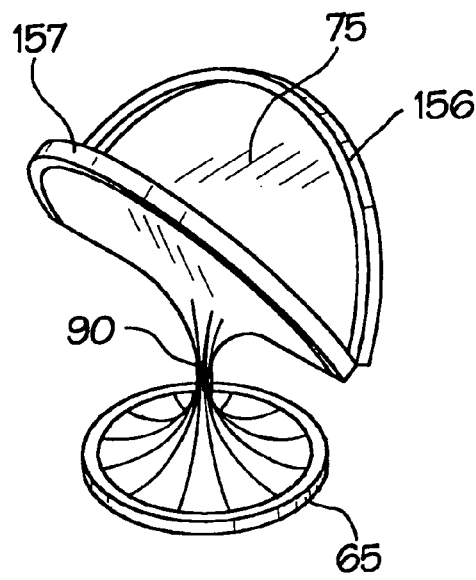
FIG. 7B illustrates the folded member in an opening condition.
Figure 7C:
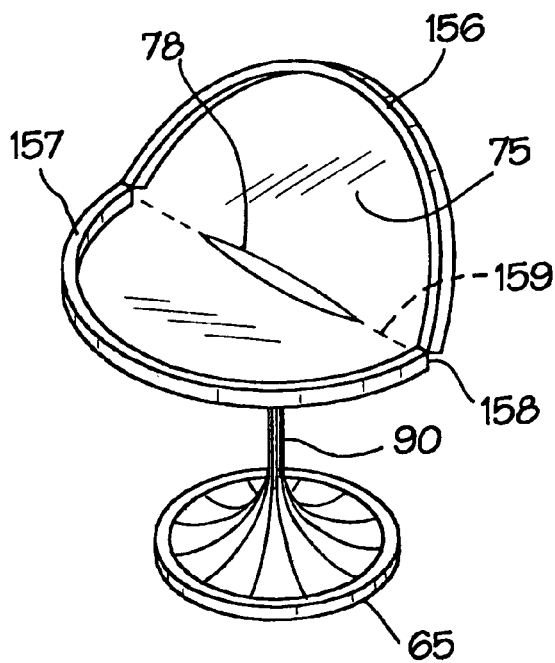
FIG. 7C shows the folded member in a half open condition.
Figure 7D:
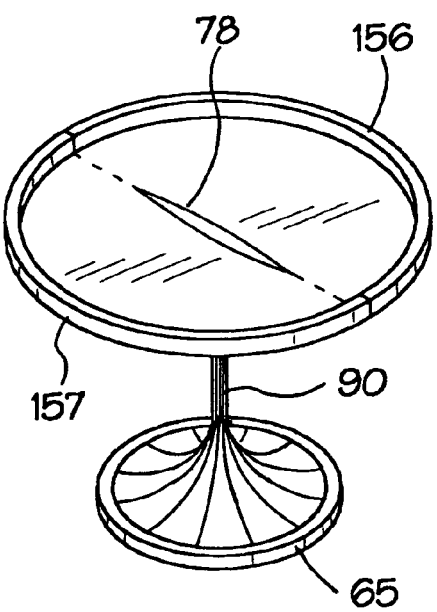
FIG. 7D shows the folded member in a fully open condition with the seal material tensioned.
Figure 8A:
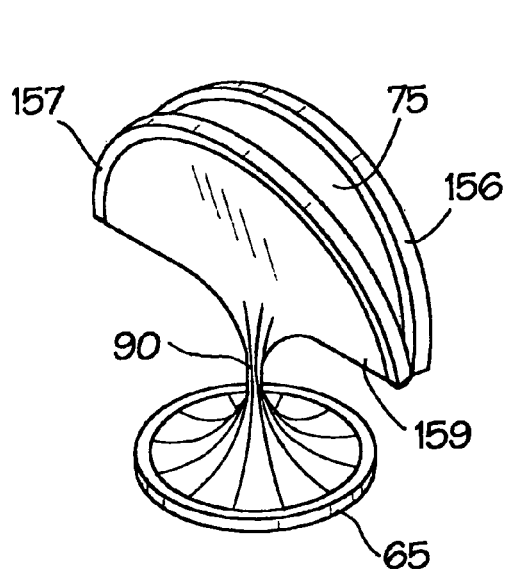
FIG. 8A illustrates an alternate embodiment of the folded retention member closed.
Figure 8B:
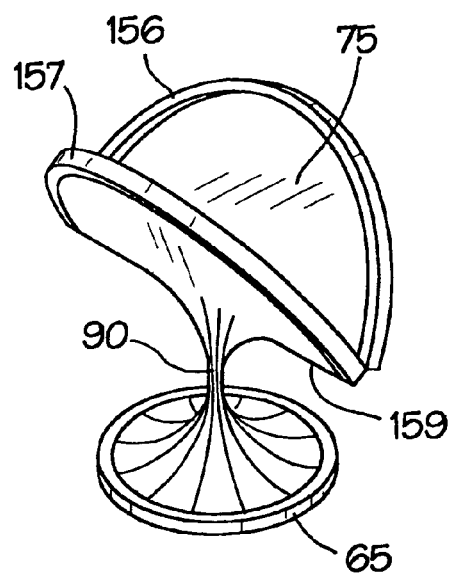
FIG. 8B illustrates the alternate embodiment partially open.
Figure 8C:
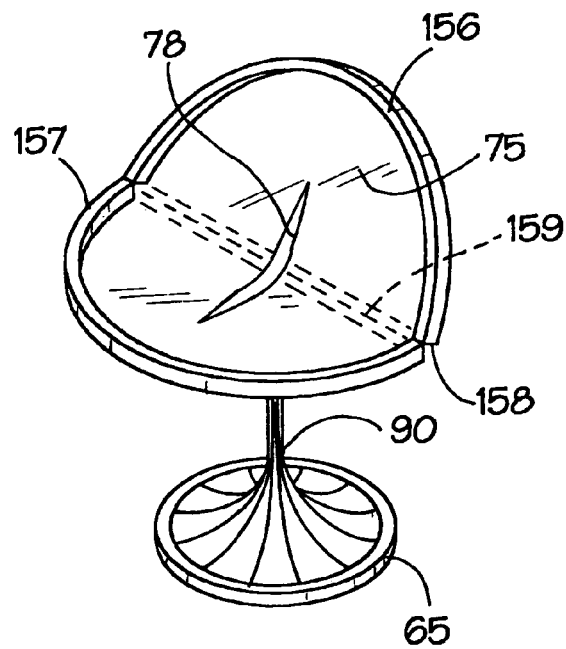
FIG. 8C shows the half open retention member having a transverse seal opening.
Figure 8D:
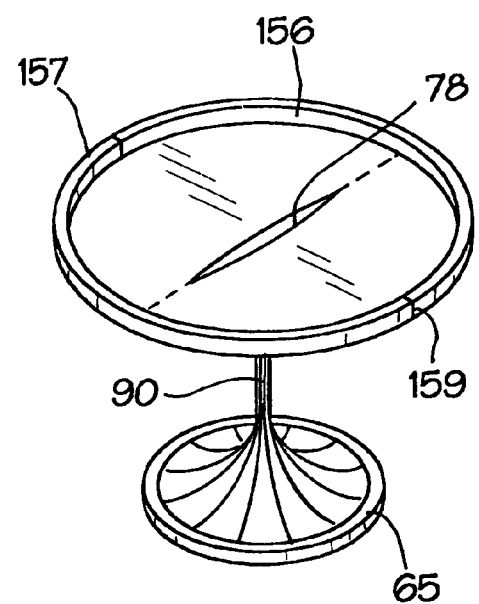
FIG. 8D shows the transverse seal opening fully tensioned along its length.

With particular reference to FIGS. 4, 5, 6, a preferred embodiment of the access device 50 has a first end 51, a second end 52 and a communicating middle portion 53. The first end 51, in a preferred embodiment, is external to a body cavity 16 and comprises an enlarged and adjustable portion 55. The exact shape of the first end portion 55 may be circular, ovoid, rectangular, square, triangular or the like. The first end portion 55 is sized and configured to be adjustable in area so that a surface 77 of a sleeve or membrane 75 is appropriately stretched or tensioned.

A preferred embodiment of the access device 50 employs an overlapping leaf spring 56 that is biased to the open condition. As opposing ends 57, 58 of the spring 56 spread apart, appropriate tension is exerted upon the sleeve/membrane 75. The applied tension causes a pulling force to be exerted through the communicating middle portion 53. This force approximates the second, internal, or distal end 52 of the access device 50 to the inner surface of the abdominal wall 18.

The second retaining portion 65 is preferably constructed of a flexible material that allows it to be inserted into the surgical incision 100 in a folded form or reduced profile. The second retaining portion 65 is preferably self-deploying or, at least, has sufficient memory to return to a preferred, somewhat circular, or pre-determined shape or condition without manipulation. The material choices for such a configuration may include flexible vinyl, rubber, silicone, or other elastomeric. The materials may also include rigid materials like rigid plastic or metal with a hinged or flexible portion.

In addition, the construction of either the first or second retention members 55 and 65, respectively, may include the use of elastomeric components that have been fitted with or have been molded to include shape memory metals, such as Nickel-Titanium (NiTinol). In any case, the second retention member 65 is easily deformable to a condition or shape that facilitates introduction into the smallest possible surgical incision 100. It must be kept in mind that the second retention member 65 must be sized and configured to retain the access device 50 in place during the rigors of an active surgical procedure, and do so without causing tissue damage such as tissue necrosis or abrasion. A preferred embodiment of the second retention member 65 comprises a ring 66 of soft silicone or vinyl with an internal, encapsulated or insert molded Nickel-Titanium support ring. This embodiment may be introduced in a very deformed condition and will subsequently recover the preferred shape and size upon completion of introduction into the body cavity 16.

As an alternative, the super-elastic and shape-memory properties of Nickel-Titanium may be drawn from temperature transition properties of the alloy. For instance, the second retention member 65 may be cooled to a temperature where the ring 66 is easily, deformable to a high degree, then, as the alloy warms to body temperature, the retention member 65 returns to a programmed shape, size or configuration.

The sleeve/membrane portion 75 is shaped by the tension between the first retention member 55 and the second retention member 65. The sleeve/membrane 75 may initially define an orifice 78 which may be a slit or a hole or the like that communicates between the exterior and the interior of the body cavity 16 through a lumen 80. The lumen 80 exhibits a first condition when the sleeve/membrane 75 is not under tension and a second condition when the sleeve/membrane 75 is under tension.

In a preferred embodiment, the tensioning of the sleeve/membrane 75 adjusts the lumen 80 to a preferred size and configuration. Such a configuration might be the creation of the radiused, funnel-shaped orifice 78 transitioning to the smaller diameter in the middle portion 53 and again transitioning to a funnel-shaped enlargement 67 distally at the second retention member 65.

The material of a preferred embodiment of the sleeve/membrane 75 may include a non-distensible or non-elastic material such as polyethylene, polyurethane or reinforced elastomeric. The choice of polyethylene for the sleeve/membrane 75 provides the surface 77 with nearly friction-free characteristics against most glove materials. Since the polyethylene material is non-elastic, the sleeve/membrane 75 will fold into discrete "fan-fold" segments 79. Such a condition will allow the material of the sleeve/membrane 75 to be compressed radially by the adjacent body tissue so that it forms a throat 90 or nearly occluded middle portion 53 when no hand or instrument is present within the lumen 80 of the device 50. Thus, in the absence of the hand or instrument, the throat functions as a zero seal. When a hand or instrument is present within the lumen 80, the fan-folded material at the throat 90 of the sleeve/membrane 75 yields to the size and shape of the inserted hand or instrument yet forms an occlusive instrument seal. Bearing in mind that the normal pneumoperitoneum is about 0.18 to 0.28 psi, the throat 90 of the present invention is adequate to form both the zero seal and the instrument seal.

The embodiment of FIG. 5 is similar to that of FIG. 4 except that the membrane 75 in proximity to the first retention member 55 has the configuration of a septum. In this case, the orifice 78 is formed as a slit which transitions into the throat 90 of the device. Fan-fold segments 79 extend to the ends of the slit or orifice 78 in this embodiment of FIG. 5. These fan-fold segments 79 are absent in the embodiment of FIG. 6.

With reference to FIGS. 7A–D, a preferred embodiment of the surgical access device 50 of the present invention comprises a first retention member 155 that is folded so that it resembles a taco. The folding of the first retention member 155 relaxes the member 75, allowing the second retention member 65 to be easily inserted into a surgical incision 100 (FIG. 2). The subsequent unfolding of the first retention member 155, for example, by forcing apart a pair of separable members 156, 157, results in a stretching of the sleeve/membrane 75. In this position, the two members 156, 157 of the first retention member 155 are locked in a single plane or flattened condition with the sleeve/membrane 75 in tension.

In a preferred embodiment of the folded first retention member 155 the orifice 78 is elongate and in line with a fold 159 of the sleeve/membrane 75 as well as a pair of hinged portions 158 of the first retention member 155. In an alternative embodiment illustrated in FIGS. 8A–8D, the orifice 78 that is elongate and transverse to both the fold 159 of the sleeve/membrane 75 and the hinged portions 158 of the first retention member 155.

With reference to FIGS. 9–17, a surgical access device 50 is shown with the first retention member 155; however, in this case the member 155 is adjustable in area or circumference In this embodiment, the two separable members 156, 157 of the first retention member 155 may be separated along a common plane by a pair of actuating adjusting sleeves 200, 220 operating against adjusting screws 210, 230. This action will place the sleeve/membrane 75 under tension so as to prepare the orifice 78 for use. There may be a several of the adjusting members 200, 220, for example, two, three, four, or more, that cooperate to stretch the sleeve/membrane 75. This stretching may be uniform or non-uniform.

Specifically referring to FIGS. 11, 12, a further embodiment of the surgical access device 50 is shown to have at least one hinge 260 that permits the separate members 156, 157 to pivot on each other in opposing directions upon application of a spreading force. In this case, the spreading force is applied by rotation of a jackscrew and thumb-wheel combination 265. The resulting non-uniform spreading force causes the orifice 78 to assume a preferred condition.

Figure 14:
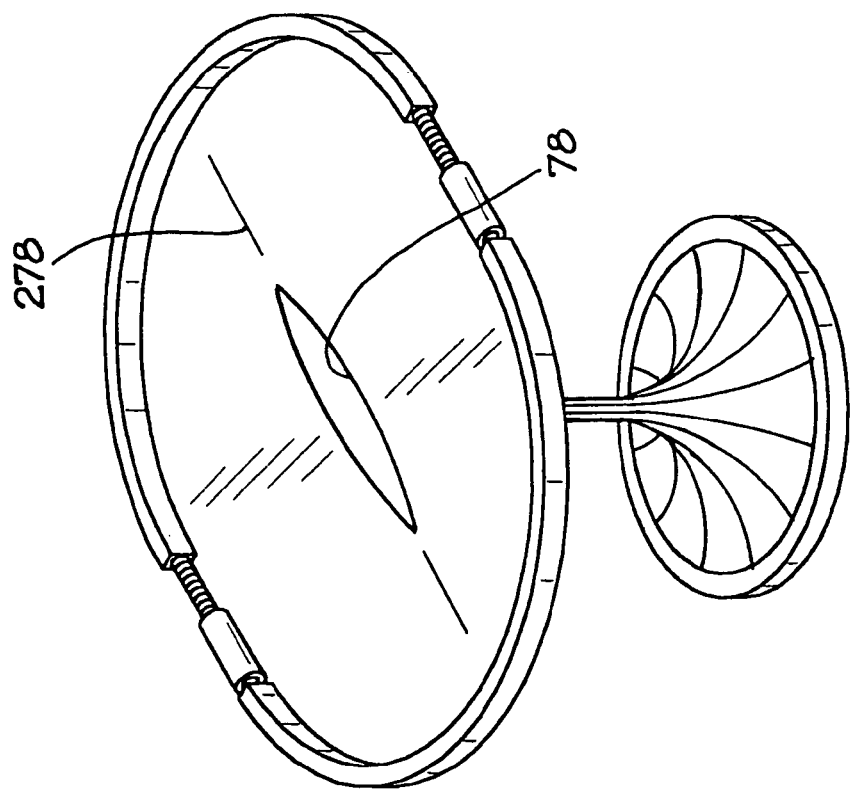
FIG. 14 shows the retention member where the seal member is under maximum tension.
Figure 13:
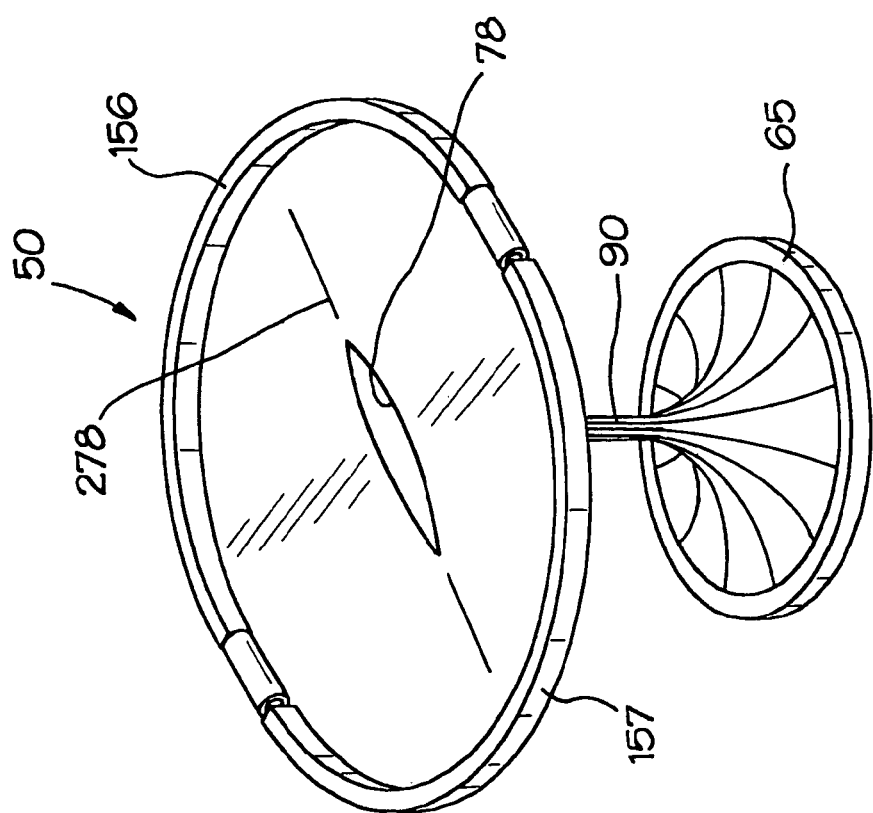
FIG. 13 shows the retention member having two jackscrew adjustments and having the seal member in a transverse position and under minimum tension.

With reference to FIGS. 13, 14, there is shown another embodiment of the surgical access device 50 according to the present invention wherein the elongate orifice 78 is positioned so as to be stretched along its lengthwise midline 278. This configuration causes the orifice 78 to assume a more closed natural condition than would be the case wherein the elongate orifice 78 is transverse to the stretching moment. A combination of in-line and transverse stretching of the sleeve/membrane 75 and the orifice 78 can result in a more symmetrical or uniform opening of the orifice 78.

Figure 16:
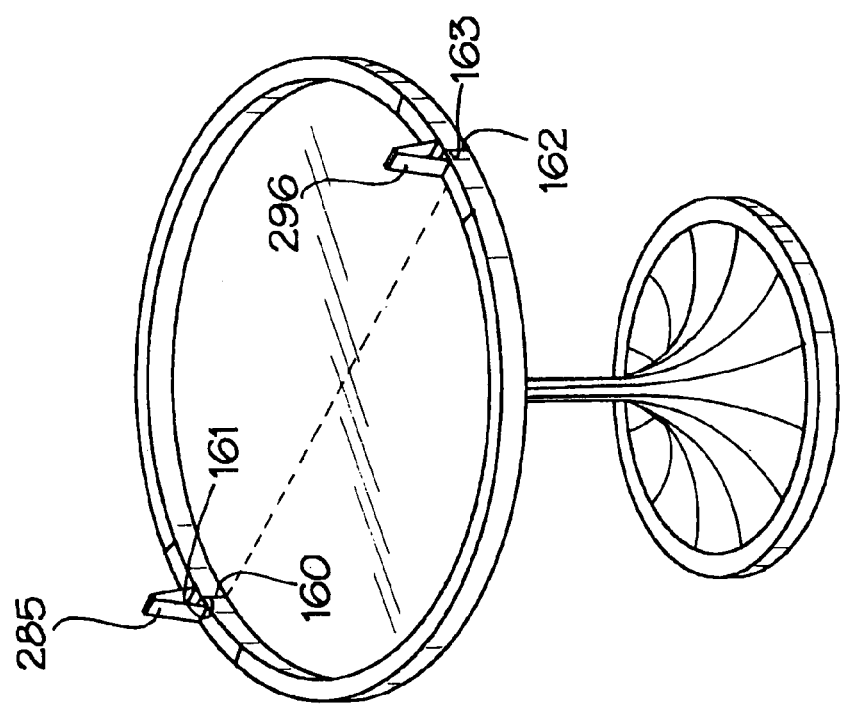
FIG. 16 shows the detente spacers in an over-center or locked position and applying tension to the seal member.
Figure 15:
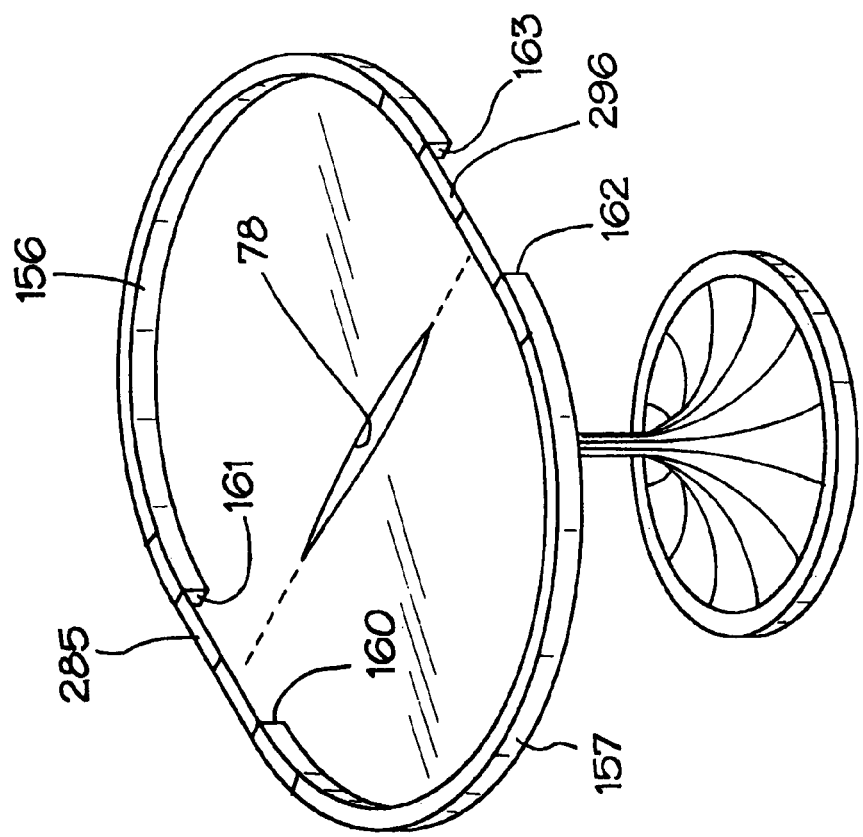
FIG. 15 illustrates an embodiment of the retention member wherein the tensioning of the seal member is provided by detente folding spacers.

Referring now to FIGS. 15, 16, another embodiment of the surgical access device 50 is shown, according to the present invention. In this embodiment the separable members 156 and 157 are moveable in a single plane between an expanded position illustrated in FIG. 15 and a contracted position illustrated in FIG. 16. In this case, the separable member 156 has ends 161 and 163 while the separable member 157 has ends 160 and 162. Folded separation members 285 and 296 are disposed between the ends 160, 161, and the ends 162, 163, respectively. In the compressed state of the separable members 156, 157, the separable members 285 and 296 are in a folded condition with the first ends 160 and 162 abutting the ends 161 and 163, respectively. When the separable members 156 and 157 are spread to the expanded state illustrated in FIG. 15, these separation members 285 and 296 are moved to an unfolded, flattened or over-centered condition as illustrated in FIG. 16. In this condition, the separation members 285 and 295 maintain the separable members 156 and 157 in the expanded state thereby stretching the membrane 175.

An elongate orifice 78 may be orientated either in-line or transverse to the direction of stretch. An additional embodiment of the surgical access device 50 may comprise a plurality of the foldable separation members 285, 296 wherein the stretching of the sleeve/membrane 75 is more or less uniform. The foldable separation members 285, 295 may be constructed of metal, with or without a discrete hinge, or plastic having either discrete or "living" hinges.

Figure 17:
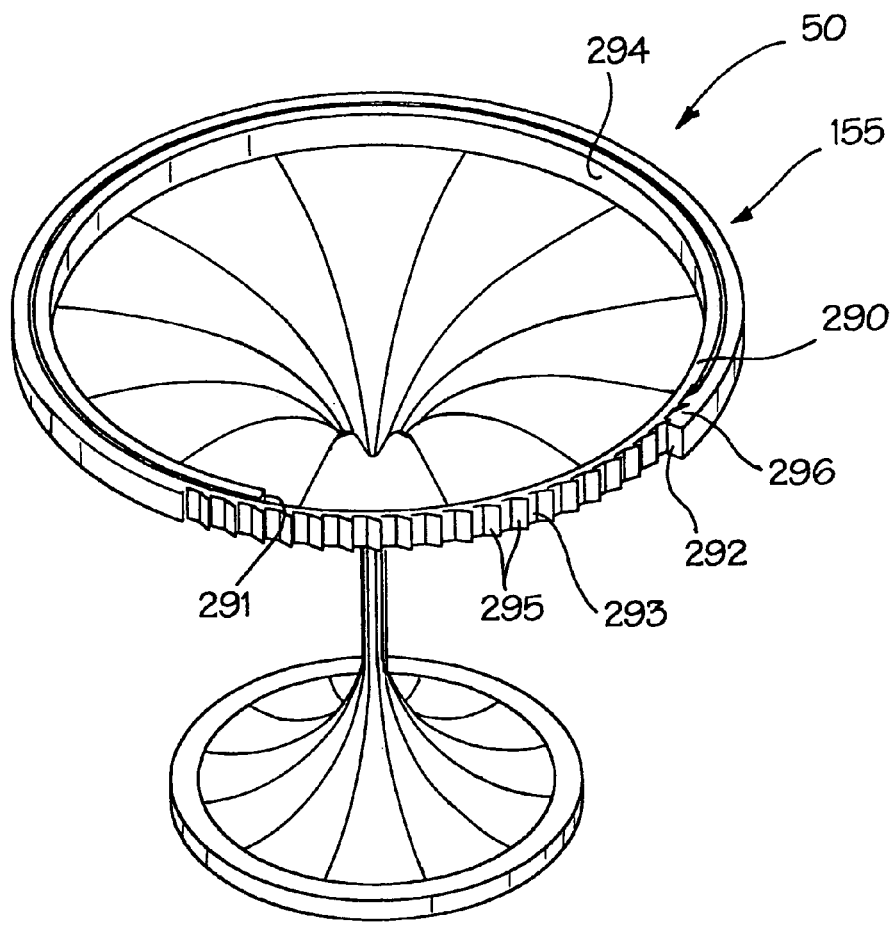
FIG. 17 is an oblique view of the external retention member having a ratchet for holding the seal member at a preferred tension.

FIG. 17 depicts a further embodiment of the surgical access device 50 according to the present invention. In this case, the first retention member 155 comprises a length of rigid or semi-rigid material formed into a hoop or coil 290. This coil 290 has opposing ends 291 and 292 as well as an outer surface 293 and an inner surface 294. When the ends 291, 292 are spread relative to each other, the coil 290 assumes a larger diameter and area so that the tension upon the attached sleeve/membrane 75 is increased.

The position of the coil ends 291 and 292 can be maintained by a series of ratchet teeth 295 and an associated ratchet pawl 296. In the illustrated embodiment, the ratchet teeth 295 are formed on the outer surface 293 and the ratchet pawl 296 is formed on the end 292. Alternatively, a second series of ratchet teeth can be formed on the inner surface 294, and an associated second ratchet pawl can be formed on the end 291. This double-ended, double-sided ratchet configuration results in a very large distention potential for the first retention member 155 and, concomitantly, the sleeve/membrane 75.

In this embodiment, the first retention member 155, as well as the ratchet teeth 295, and the ratchet pawl 296, are preferably constructed of a rigid plastic material such as polycabonate, ABS, PBC or other filled or non-filled material. In a further embodiment, the first retention member 155 may be formed from a metal so that it is sterilizable and reusable. Such an embodiment may still include the disposable sleeve/membrane 75 and the second retention member 65.

With reference now to FIGS. 18, 19, 20, 21, a surgical access device 50 according to the present invention is shown having an inflatable or fillable first retention member 300, and a malleable, foldable or otherwise deformable second retention member 65. In a preferred embodiment, the inflatable or fillable retention member 300 comprises a closed, hollow structure 310 which may be circular or toroidal. The hollow structure 310, when un-inflated or un-filled exerts very little, if any, stretching or tensioning force upon the sleeve/membrane 75. When the hollow structure 310 is inflated, however, it assumes a larger diameter and area which results in the desired stretching or tensioning of the sleeve/membrane 75. Preferred embodiments of the hollow structure 310 can be formed from either elastic or non-distensible materials.

Figure 19:
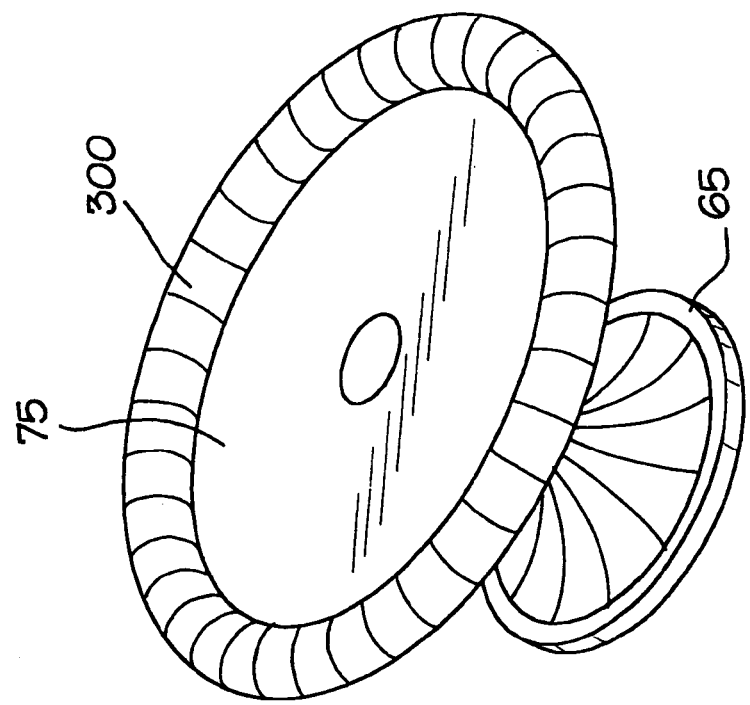
FIG. 19 shows the inflatable retention member fully inflated and tensioning the sealing member to provide sealing pressure.
Figure 18:
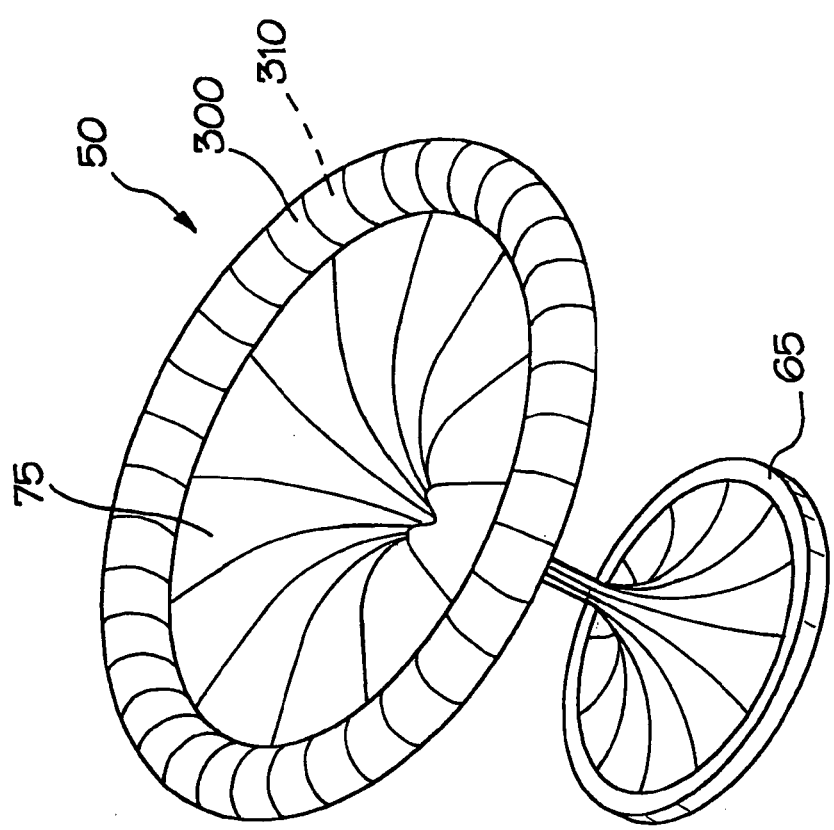
FIG. 18 illustrates an alternate embodiment of the present invention wherein the external retention member is an un-inflated but inflatable or fillable hollow torrus.

Similarly the sleeve or membrane 75 can be formed from an elastic material although in a preferred embodiment the membrane 75 is non-distensible. In this embodiment, expansion of the hollow structure 310 also stretches the sleeve/membrane 75 so that the throat 90 of the access device 50 is also placed under tension. This tensioning of throat 90 which connects the first retention member 300 and the second retention member 65, causes the second retention member 65 to be appropriately drawn into sealing engagement with the interior surface of the abdominal wall 18 (FIG. 1). This will result in a gas-tight seal around the access device 50. In the embodiment of FIG. 19, the membrane 75 is in the form of a septum.

Figure 21:
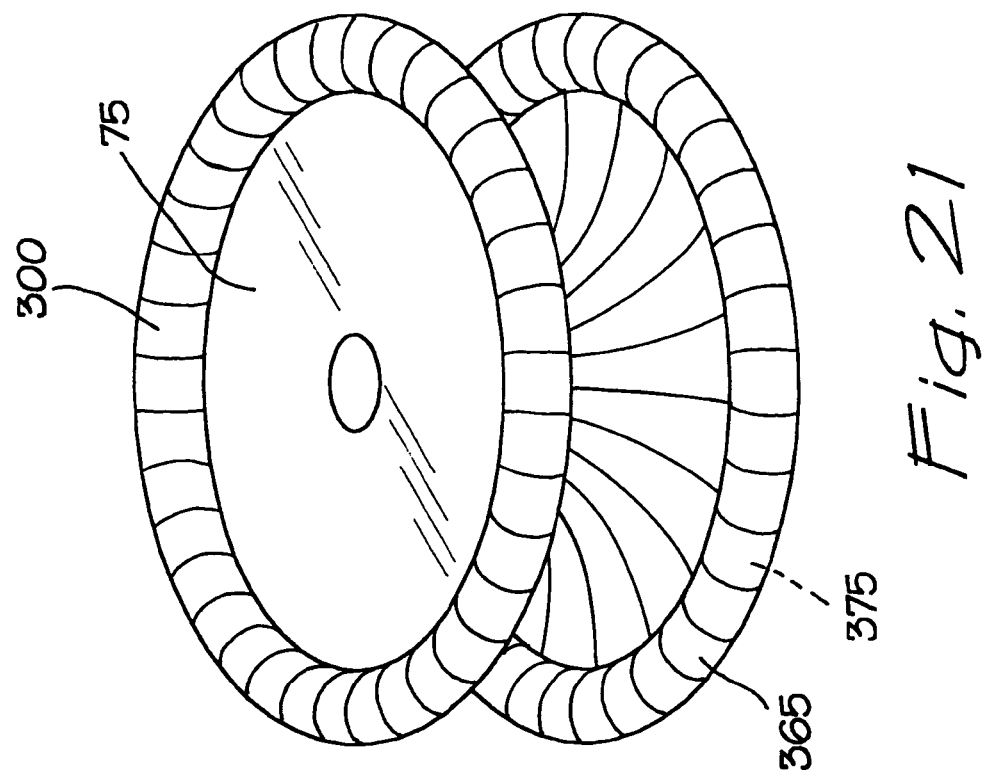
FIG. 21 shows the two inflatable retention members fully inflated and the seal member fully tensioned.
Figure 20:
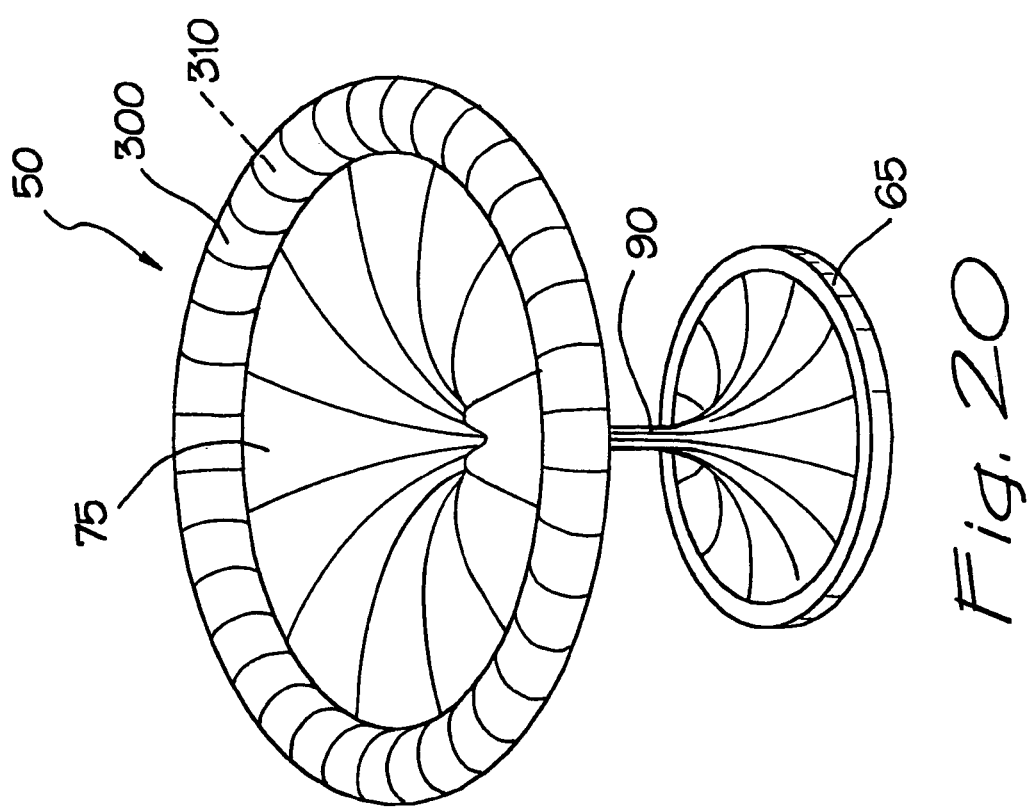
FIG. 20 illustrates the present invention having two un-inflated but inflatable retention members and the seal member at minimum tension.

With attention drawn specifically to FIGS. 20, 21, there is shown a surgical access device 50 according to the present invention wherein a first retention member 300 includes the inflatable or fillable structure 310, and a second retention member 365 also includes an inflatable or fillable structure 375. The second retention member 365, when un-inflated or un-filled may be easily inserted through an incision 100 into a body cavity 16 and subsequently inflated or filled to assume a more-or-less rigid or definite shape and configuration within the body cavity 16. The first retention member 300 may then be inflated or filled to provide the external retention and the concurrent stretching or tensioning of the sleeve/membrane 75. Although it is apparent that the sleeve/membrane 75 can also be formed with a double wall structure that is inflatable, this is not the case with the embodiments of FIGS. 20 and 21. In these illustrated embodiments, the sleeve/membrane 75 that connects the two inflatable or fillable retention members 300, 365, is formed of a single layer or thickness of non-dispensable or non-elastic material. With this construction, the membrane 75 is not inflatable and relies on a minimum of intrusive material along the middle portion or throat 90 and through the incision 100. At this throat 90 of the access device 50, the sleeve/membrane 75 remains smooth, lubricious, thin, and non-bulky.

Figure 23:
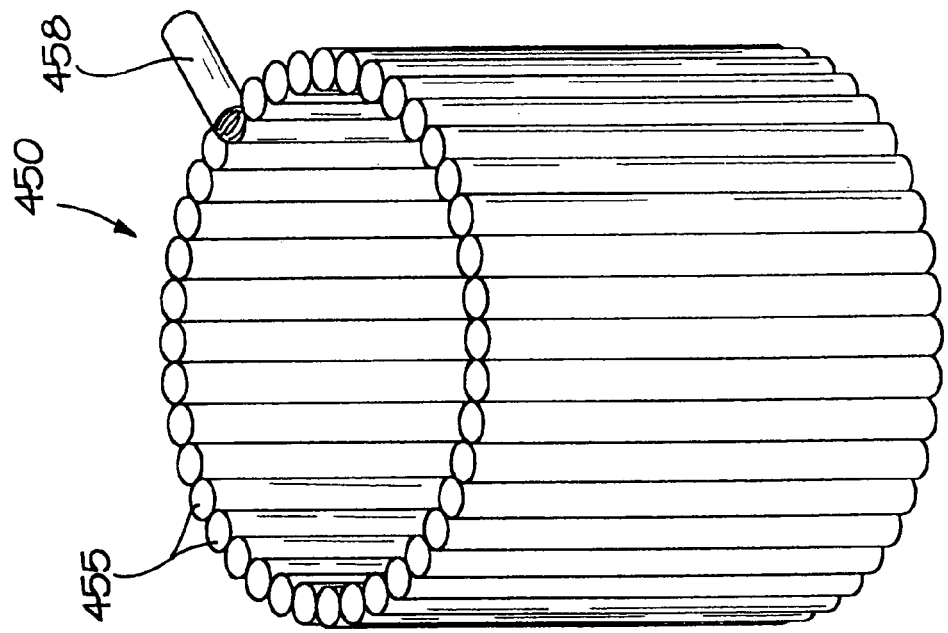
FIG. 23 shows the alternate embodiment in an inflated condition and shaped as would be the case if the device were inserted within a surgical incision.
Figure 22:
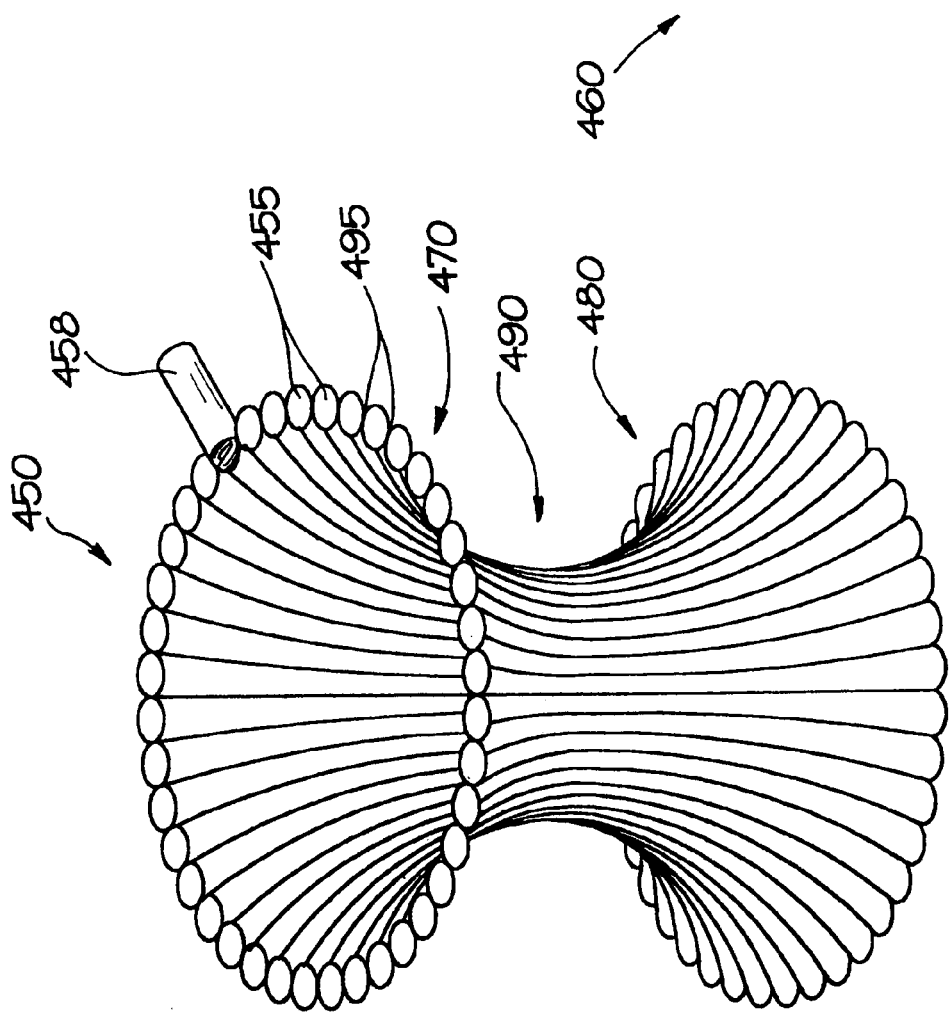
FIG. 22 illustrates an alternate embodiment of the present invention where the un-inflated retention members and the seal portion are integrally formed of connected tubular segments.

An additional embodiment of the access device 50 of the present invention is shown in FIGS. 22, 23 wherein an open-ended, generally cylindrical sleeve 450 is constructed of a plurality of axially aligned, communicating, hollow, inflatable, fillable members 455. The communicating members 455 are inflatable or fillable by means of an inflation tube 458. Particularly when uninflated, the generally cylindrical shape (FIG. 23) of the access device 450 may be easily distorted so that a distal end 460 may be placed through the surgical incision 100 and the abdominal cavity 16. As the access device 450 is inflated or filled, it assumes an "hourglass" shape, and develops a first retention portion 470 and a second retention portion 480 joined by a middle section 490.

A non-distensible or non-elastic material is also stipulated for use in this preferred embodiment so that friction is minimized, and so that the material of the middle section 490 does not gather or fold as a gloved hand or large instrument is repeatedly inserted and withdrawn through the access device 450.

In the illustrated embodiment, the individual inflatable or fillable members 455 form axial chambers and abutments 495 which prevent material motion and also minimize surface contact between a gloved hand and the material which forms the seal with the abdominal wall 18. The lumen of the middle section 490 may be lubricated with a thick or viscous material which can be stored along the seams of the abutting or adjoining inflatable or fillable members 455. The lubricating product may also function to perfect the instrument seal in the present of a gloved hand or instrument, or to perfect the zero seal in the absence,of the gloved hand or instrument.

With reference to FIG. 24, a surgical access device 50 according to the present invention is shown wherein a compressible helical coil member 500 forms a first retention member 550. The coil member 500 may be deformed so as to minimize the tension upon an attached sleeve/membrane 75 and a middle portion 560 thereof. A second retention member 565 may be deformed and placed, within the surgical incision 100, so that upon release or decompression of the coil 500 of the first retaining member 550 the second retaining member 565 is appropriately approximated to the interior wall of a body cavity. For packaging and shipping, the coil 500 of the first retaining member 550 may be maintained within a containment pouch, bag, box ,or the like (not shown) in its most-compact condition. In this condition, the first retaining member 550 will exert a minimum of tension upon the attached sleeve/membrane 75.

In a similar embodiment illustrated in FIG. 25, a second retaining member 563 is also provided with a second retention coil member 565. This second retaining coil member 565 may be introduced through the incision 100 in a compact configuration and subsequently released to assume an enlarged diameter. This provides the access device 50 with an increased area of contact at the inner surface of the abdominal wall 18. As the second retention coil 565 is released to assume its enlarged diameter, it also functions to stretch or tension the attached sleeve/membrane 75.

With reference to FIGS. 26, 27, there is shown a surgical access device 50 according to the present invention that is adapted to be held in position over the surgical incision 100 by, a strap or belt 600 which surrounds the abdomen 12 of the patient 10 (FIG. 1). In this embodiment, the access device 50 may include the strap or belt 600 and associated closure members or buckles 610. The access device 50 in the embodiment of FIG. 26 is illustrated as a septum seal 615. In the embodiment of FIG. 27, the access device is similar to that described with reference to FIG. 19 and designated with the reference numeral 300.

Figure 28:
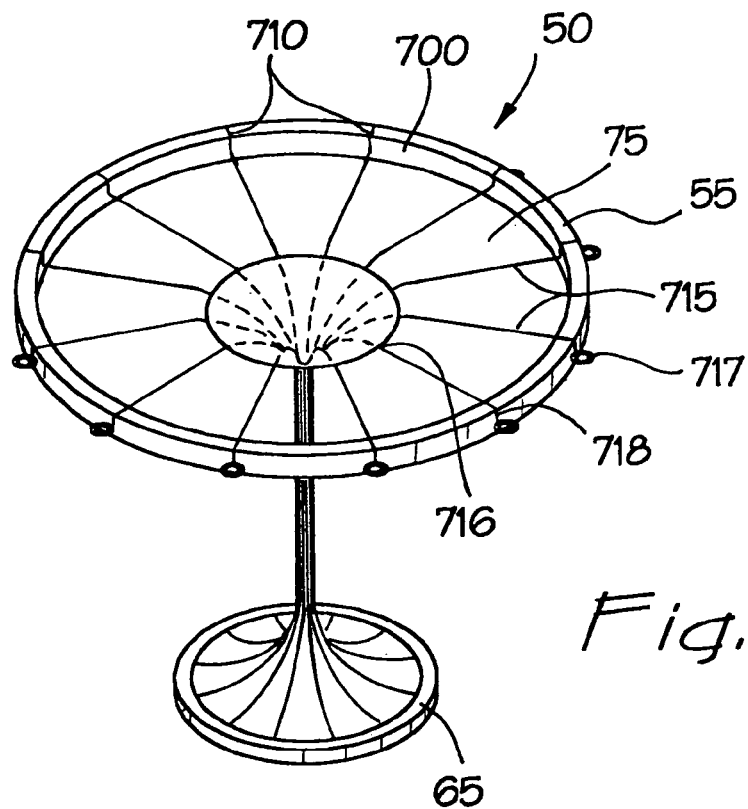
FIG. 28 illustrates an additional preferred embodiment of the present invention wherein the sleeve/membrane has tensioning tethers in a first condition.
Figure 29:
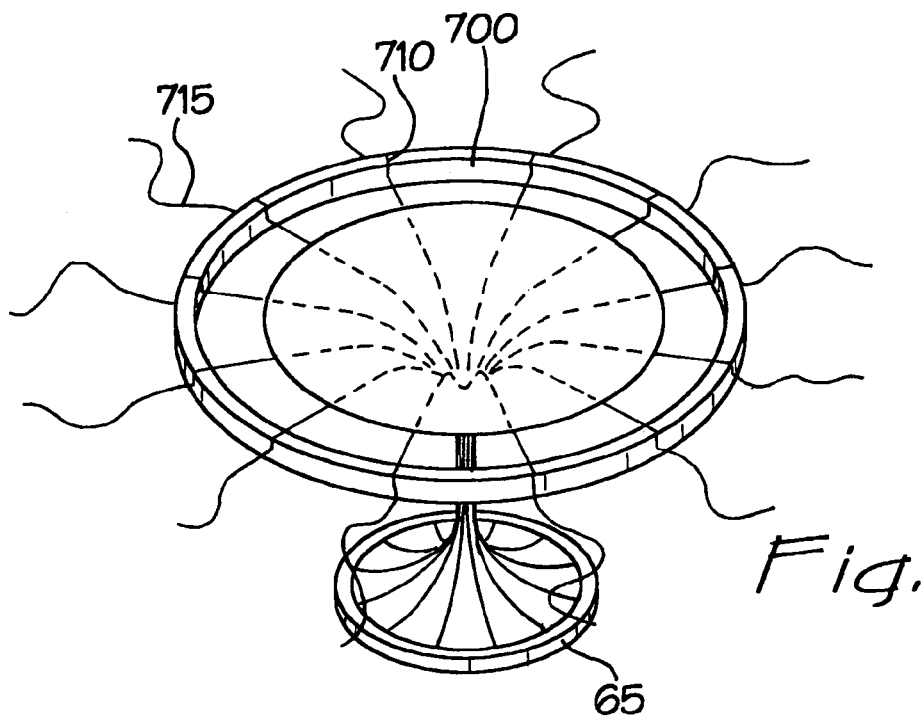
FIG. 29 illustrates the tethers in a second condition.

Turning now to FIGS. 28 and 29, the surgical access device 50 is shown with a membrane 75 extending between the first retention member 55 and the second retention member 65. In this embodiment, the first retention member 55 includes a solid, rigid ring 700 that is disposed in a plane generally perpendicular to the axis of the access device 50. On the side of the ring 700 opposite the second retaining portion 65, a plurality of slits 710 are provided which extend radially of the ring 700. In this embodiment, a plurality of tethers 715 are attached to the membrane 75 at different radial locations. The tethers 715 are attached to the membrane 75 at an inner end 16 and are provided with an enlargement feature 717 at an outer end 718. In this embodiment, the slits 710 of the ring 700 are sized and configured to engage and confine at least one of the tethers 715. In such an embodiment, the enlargement features 715 can act to prevent the tethers 715 from being drawn back through the slits 710. The enlargement feature 717 can also function as handles facilitating engagement of each of the tethers 717, as it is drawn outwardly through the associated slit 710 to tension the membrane 75.

Figure 30:
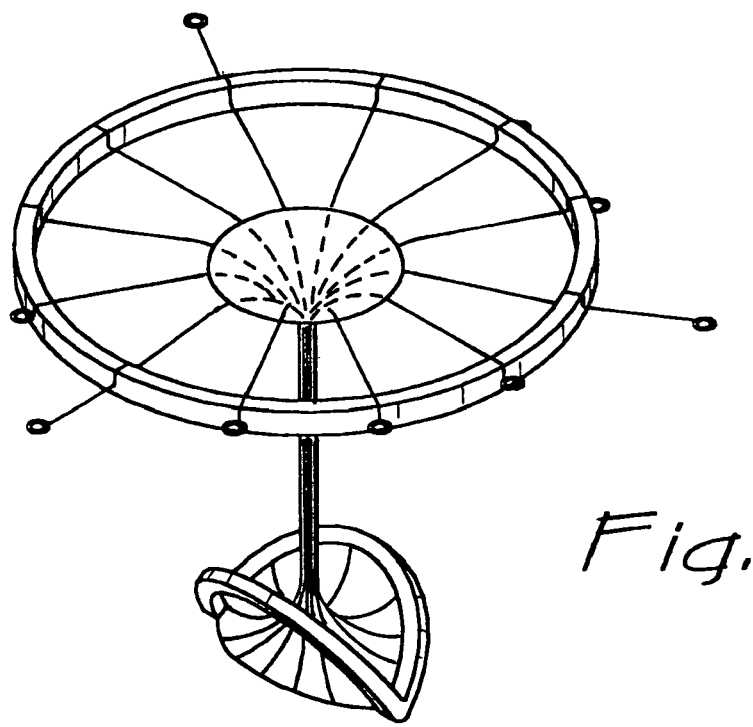
FIG. 30 illustrates the tethers in an irregular, non-uniform configuration.
Figure 31:
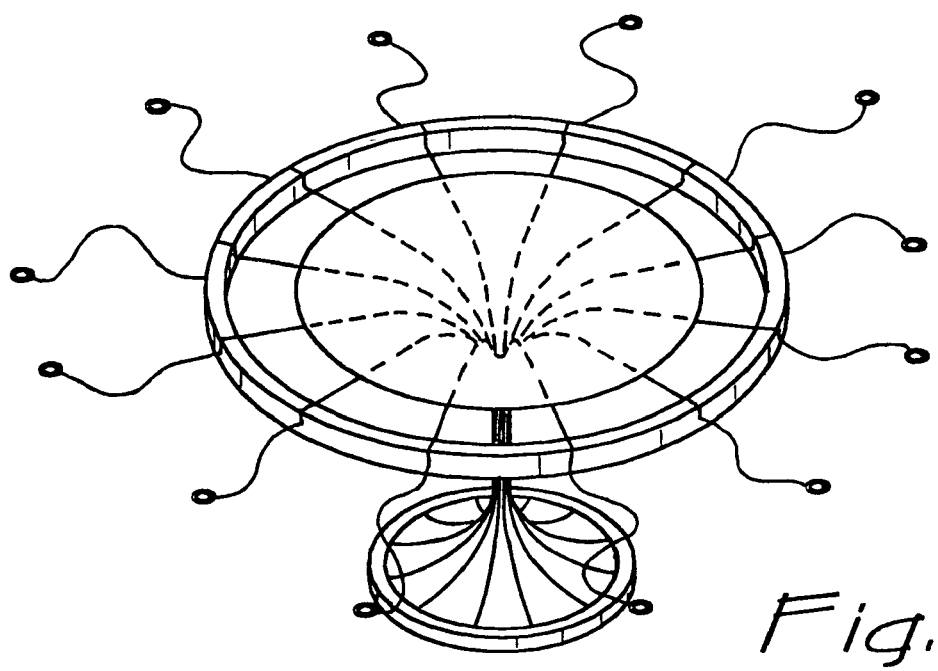
FIG. 31 illustrates the tethers in a regular, uniform configuration.

In such an embodiment, it may be desirable to form the slits 710 so that they are tapered toward the bottom of the slit 710. This will facilitate compression of the associated tether 715 to increase the frictional engagement between the tether 715 and the ring 700. In this manner, the tethers 715 can be collectedly adjusted to provide the membrane 75 with the desired shape and seal characteristics. The membrane 75 can be released from the ring 700 by merely lifting the tethers 715 to disengage their associated slits 710. In FIG. 30, the tether 715 is tensioned non-uniformly to provide the membrane 715 with an irregular shape. This configuration can be compared with that illustrated in FIG. 31 wherein the tethers are tensioned uniformly to provide the membrane 75 with a uniform configuration.

Figure 32:
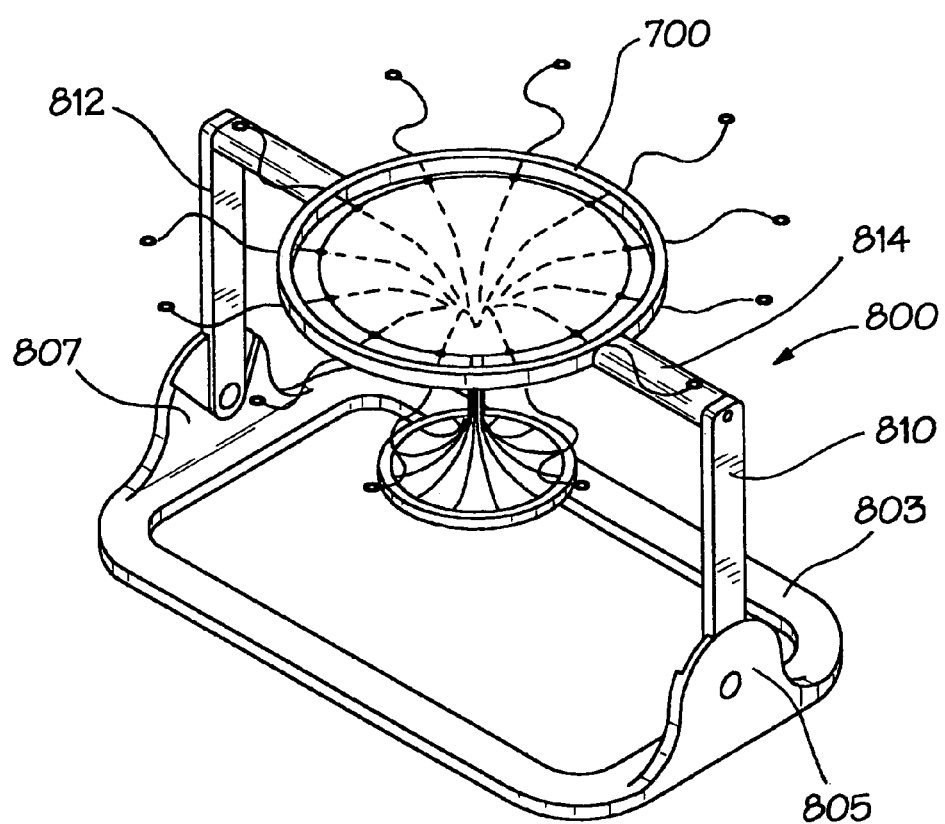
FIG. 32 is a perspective view of an access device in combination with a stabilizing platform.

In FIG. 32, the access device 50 is illustrated in combination with a stabilizing platform 800. Initially, it will be noted that the access device 50 which is illustrated, is that described generally with reference to FIGS. 28-31. However, it will be apparent that the stabilizing platform 800 can be adapted to receive and function with any of the foregoing embodiments of the access device 50, in order to achieve the advantageous discussed below.

In this embodiment, the stabilizing platform 800 includes a base having a generally planer configuration with a pair of support flanges 805 and 807 extending perpendicular on opposing sides of the base 803. A pair of upstanding arms 110 and 112 are pivotally, and perhaps releasably attached to the associated flanges 805 and 807. A cross member 814 is pivotally and perhaps releasably connected between the arms 810 and 812. This cross member 814 in a preferred embodiment is perpendicular to the arms 810 and 812 and parallel to the plane of the base 803. The access device 50 is supported by the cross member 814, with its axis 816 generally perpendicular to the cross member 814. With this orientation, the first retention member 855, represented by the ring 700, is disposed in a plane which may be pivoted relative to the upstanding arms 810, 812, as well as the base 803.

In operation, the base 803 is disposed beneath the patient 10 (FIG. 1) in contact with the back of the patient 10. The upstanding arms 810 and 812 can then be mounted to the flanges 805 and 807, respectively, on either side of the patient 10. The cross member 814 can then be attached to the arms 810 and 812.

The support platform 800 can be of considerable advantage in a hand-assisted laparoscopic procedure which requires that a human hand being inserted and withdrawn several times while maintaining the abdominal pressure or pneumoperitoneum. As noted, the sealing port or throat 90 (FIG. 4) of the access device 50 must tightly fit around the wrist or arm of the surgeon. When the hand of the surgeon is removed, the throat 90 must close tightly to form a zero seal. This closed sealing attachment to the hand or arm of the surgeon can cause the abdominal wall 18 (FIG. 1) to change in shape and particularly in elevation as the hand is inserted and removed. If the access device 50 is directly attached to the abdominal wall 18, this movement of the wall 18 can result in movement of the access device 50 causing other surgical instruments, such as a laparoscope, to be moved or displaced. It is the purpose of the stabilizing platform 800 to support the access device 50 independently of the abdominal wall 18. With this stabilization, movement of the surgeon's hand through the abdominal wall 18 will be less apt to move the access device 50. This greatly stabilizes the surgical field and particularly the instruments inserted through the access device 50. Appropriate pivoting of the cross member 814 and the arms 810 and 812 enable the access device 50 to be swiveled to a position appropriate to patients of various size and weight. In an alternative embodiment, the base may be formed as part of a surgical table with at least one support member, such as the arms 810, 812, extending from one or both sides of the patient to support the cross member 814.

Given the many embodiments disclosed herein for the access device 50, many other embodiments will now become apparent with changes in structure or materials. For that reason one is cautioned not to limit the scope of the invention only to the disclosed embodiments, but only with reference to the following claims.

What is claimed is:

1. A surgical access device adapted to facilitate access through an incision in a body wall and into a body cavity of a patient, the body wall having an inner surface and an outer surface, the device comprising;
   a first retention member sized and configured to surround the incision in proximity to the outer surface of the body wall, the first retention member including a hoop with a first end and a second end;
   a second retention member sized and configured to surround the incision in proximity to the inner surface of The body wall;
   a membrane extending between the first retention member and the second retention member, the membrane forming a throat adapted for disposition through the incision, the membrane forming a first funnel extending from the first retention member into the throat, and the membrane forming a second funnel extending from the second retention member into the throat; and
   the throat of the membrane having characteristics for forming an instrument seal in the presence of an instrument and a zero seal in the absence of an instrument;
   wherein the hoop is provided with a series of ratchet teeth and the first end includes a ratchet pawl.

2. The surgical access device recited in claim 1, where the incision has a length and the first retention member comprises a ring having a diameter greater than the length of the incision.

3. The surgical access device recited in claim 2, wherein the ring has a variable diameter.

4. The surgical access device recited in claim 1 wherein the second end includes a ratchet pawl.

5. A surgical access device adapted to facilitate access through an incision in a body wall and into a body cavity of a patient, the body wall having an inner surface and an outer surface, the device comprising;
   a first retention member sized and configured to surround the incision in proximity to the outer surface of the body wall;
   a second retention member sized and configured to surround the incision in proximity to the inner surface of the body wall;
   a membrane extending between the first retention member and the second retention member, the membrane forming a throat adapted for disposition through the incision, the membrane forming a first funnel extending from the first retention member into the throat, and the membrane forming a second funnel extending from the second retention member into the throat;
   the throat of the membrane having characteristics for forming an instrument seal in the presence of an instrument and a zero seal in the absence of an instrument; and
   at least one strap fixed to the first retention member, the strap being sized and configured for disposition around the patient to hold the first retention member in proximity to the outer surface of the body wall.

6. The surgical access device recited in claim 5, where the incision has a length and the first retention member comprises a ring having a diameter greater than the length of the incision.

7. The surgical access device recited in claim 6, wherein the ring has a variable diameter.

8. The surgical access device recited in claim 5, wherein the first retention member comprises a hoop with a first end and a second end.

9. The surgical access device recited in claim 8, wherein the hoop is provided with a series of ratchet teeth and the first end includes a ratchet pawl.

10. The surgical access device recited in claim 9, wherein the second end includes a ratchet pawl.

11. A surgical access device adapted for disposition through an incision in a body wall, having an outer surface and an inner surface, the device comprising:
 a first retention member adapted for disposition in proximity to the outer surface and surrounding the incision;
 a second retention member adapted for disposition in proximity to the inner surface and surrounding the incision;
 a membrane stretchable between the first retention member and the second retention member to form a working channel, having a shape dependent on the shape of the first retention member;
 the first retention member comprising a ring having a first section with a first end and a second end, and a second section with a third end moveable relative to the first end of the first retention member and a fourth end moveable relative to the second end of the first retention member;
 a coupler disposed between the first end of the first section and the third end of the second section, the coupler being operable to vary the distance separating the first end and the third end to control the shape of the working channel.

12. The surgical access device recited in claim 11, wherein the coupler is a first coupler and the device further comprises:
 a second coupler disposed between the second end of the first section and the fourth end of the second section; and
 the second coupler being operable to vary the distance separating the second end of the first coupler and the fourth end of the second coupler to control the shape of the working channel.

13. The surgical access device recited in claim 12, wherein:
 the working channel has the configuration of a longitudinal slit; and
 the slit is oriented generally perpendicular to an Imaginary line drawn between the first coupler and the second coupler.

14. The surgical access device recited in claim 12, wherein:
 the working channel has the configuration of a longitudinal slit; and
 the slit is oriented generally parallel to an imaginary line drawn between the first coupler and the second coupler.

15. The surgical access device recited in claim 11, further comprising:
 a hinge disposed between the second end of the first section and the fourth end of the second section, the hinge being operable with the coupler to control the shape of the working channel.

16. The surgical access device recited in claim 11, wherein the coupler includes:
 a screw carried by the first end of the first section;
 a threaded sleeve carried by the third end of the second section; and
 the sleeve being rotatable to engage the screw and vary the distance separating the first end and the third end.

17. The surgical access device recited in claim 16, wherein the sleeve comprises a jack-nut.

18. A surgical access device adapted to facilitate access through an incision in a body wall and into a body cavity of a patient, the body wall having an inner surface and an outer surface, the device comprising;
 a first retention member sized and configured to surround the incision in proximity to the outer surface of the body wall;
 a second retention member sized and configured to surround the incision in proximity to the inner surface of the body wall;
 a membrane forming a working channel between the first retention member and the second retention member to provide access through the incision and into the body cavity, the membrane having shape dependent upon the shape of the first retention member; and
 the first retention member having the shape of a toroid including a circumferential spring and having a volume variable to change the shape of the first retention member with a corresponding change in the shape of the working channel.

19. The surgical access device recited in claim 18, wherein the toroid of the first retention member is inflatable to change the shape of the first retention member and the working channel.

20. The surgical access device recited in claim 18, wherein the toroid of the first retention member includes a self expanding foam.

21. A surgical access device adapted to facilitate access through an incision in a body wall and into a body cavity of a patient, the body wall having an inner surface and an outer surface, the device comprising;
 a first retention member sized and configured to surround the incision in proximity to the outer surface of the body wall;
 a second retention member sized and configured to surround the incision in proximity to the inner surface of the body wall;
 a membrane forming a working channel between the first retention member and the second retention member to provide access through the incision and into the body cavity, the membrane having shape dependent upon the shape of the first retention member;
 the first retention member, including a ring with a plurality of retention stations; and
 a plurality of tethers attached to the membrane and coupling the membrane to the ring, each of the tethers releasably engaging an associated one of the retention stations at a particular position along the tether providing the membrane with a desired shape.

22. The access device recited in claim 21, wherein at least one of the retention stations includes portions of the ring defining a groove sized and configured to receive and releasably hold the associated tether at the particular position along the tether.

23. The surgical access device recited in claim 22, wherein the groove is generally V-shaped.

* * * * *

UNITED STATES PATENT AND TRADEMARK OFFICE
CERTIFICATE OF CORRECTION

| | |
|---|---|
| PATENT NO. | : 7,052,454 B2 |
| APPLICATION NO. | : 10/399057 |
| DATED | : May 30, 2006 |
| INVENTOR(S) | : Scott Taylor and Charles C. Hart |

It is certified that error appears in the above-identified patent and that said Letters Patent is hereby corrected as shown below:

<u>Title Page,</u>

Item [75], Inventor, replace "Scott Taylor, Mission Viejo, CA (US)" with
-- Scott Taylor, Mission Viejo, CA (US); Charles C. Hart, Summerville, SC (US) --

Signed and Sealed this

Twenty-second Day of August, 2006

JON W. DUDAS
*Director of the United States Patent and Trademark Office*